(12) United States Patent
Rangarajan et al.

(10) Patent No.: US 7,892,792 B2
(45) Date of Patent: Feb. 22, 2011

(54) CELLS EXPRESSING *PICHIA* CYTOCHROME C

(75) Inventors: Pundi N Rangarajan, Bangladore (IN);
Ram Rajasekharan, Bangladore (IN);
Abhishek Mohanty, Secunderabad (IN)

(73) Assignee: Indian Institute of Science, Karnataka (IN)

( * ) Notice: Subject to any disclaimer, the term of this patent is extended or adjusted under 35 U.S.C. 154(b) by 0 days.

(21) Appl. No.: 12/491,909

(22) Filed: Jun. 25, 2009

(65) Prior Publication Data

US 2010/0041099 A1    Feb. 18, 2010

(30) Foreign Application Priority Data

Jun. 27, 2008    (IN) .................. 1123/KOL/2008

(51) Int. Cl.
*C12P 21/06*    (2006.01)
*C12P 7/64*    (2006.01)
*C12N 1/00*    (2006.01)

(52) U.S. Cl. ............ 435/69.1; 435/134; 435/189; 435/254.11; 435/254.23

(58) Field of Classification Search ............ None
See application file for complete search history.

(56) References Cited

U.S. PATENT DOCUMENTS

| | | | | |
|---|---|---|---|---|
| 5,750,372 | A * | 5/1998 | Sakai et al. | 435/69.1 |
| 6,432,684 | B1 | 8/2002 | Mukerji et al. | |
| 6,699,691 | B2 * | 3/2004 | Inan et al. | 435/69.1 |

2003/0163845 A1    8/2003   Mukerji et al.

FOREIGN PATENT DOCUMENTS

| | | |
|---|---|---|
| WO | WO 00/55330 | 9/2000 |
| WO | WO 2004/104167 | 12/2004 |
| WO | WO 2005/047480 | 5/2005 |
| WO | WO 2006/033723 | 3/2006 |
| WO | WO 2006/064317 | 6/2006 |

OTHER PUBLICATIONS

Janbon et al. Yeast sequencing report. Yeast (1997) 13, 985-990.*
Bhatnagar et al. Yeast cytochrom c is a sequence-specific DNA-binding protein (2004) Biochem Biophys. Res. Comm. 321, 900-904.*
Cregg, et al., "*Pichia pastoris* as a host system for transformations", Mol. Cell Biol., 1985, vol. 5, pp. 3376-3385.
Erdmann and Kunau, "Purification and immunolocalization of the peroxisomal 3-oxoacyl-coA thiolase from *Saccharomyces cerevisiae*", Yeast, 1994, vol. 10, pp. 1173-1182.
Mumberg et al., "Yeast vectors for the controlled expression of heterologous proteins in different genetic backgrounds", Gene, 1995, vol. 156, pp. 119-122.
You, et al., "Ethanol Tolerance in the Yeast *Saccharomyces cerevisiae* Is Dependent on Cellular Oleic Acid Content", Appl. Environ. Microbiol., 2003, vol. 69, pp. 1499-1503.

* cited by examiner

*Primary Examiner*—Nashaat T Nashed
(74) *Attorney, Agent, or Firm*—Foley & Lardner LLP

(57) ABSTRACT

Described herein are recombinant yeast cells that express a cytochrome C gene the expression of which causes the recombinant yeast cells to (i) grow faster than wild type yeast cells of the same species when cultured on glucose medium, and (ii) accumulate high levels of polyunsaturated fatty acid precursor molecules or target gene expression products when grown on oleic acid.

18 Claims, 12 Drawing Sheets

FIG. 7

```
PpCytc    MPAPYEKGSEKKGATLFKTRCLQCHTVEAGGPHKVGPNLHGVFGRKSGLAEGYSYTDANK 60
ScCytc    -MTEFKAGSAKKGATLFKTRCLQCHTVEKGGPHKVGPNLHGIFGRHSGQAEGYSYTDANI 59
            ::  ** ********************  **********;***;** *********

PpCytc    RKGVEWSEQTMSDYLENPKKYIPGTKMAFGGLKKAKDRNDLITYLAKATK 110 (SEQ ID NO: 2)
ScCytc    KKNVLWDENNMSEYLTNPKKYIPGTKMAFGGLKKEKDRNDLITYLKKACE 109 (SEQ ID NO: 3)
          :*.* *.*;.**;** ****************** ********* **  ;
```

* denotes amino acid residues that are identical in PpCyt c and ScCyt c.
: denotes conserved amino acid substitutions.
. denotes semi-conserved amino acid substitutions.

FIG. 8A

```
                        10         20         30         40         50         60
                        |          |          |          |          |          |
Pichia pastoris         MPAPYEKGSEKKGATLFKTRCLQCHTVEAGGPHKVGPNLHGVEGRKSGLAEGYSYTDANK
Debaryomyces hansenii   MPAPYEKGSEKKGANLFKTRCLQCHTVEEGGPHKVGPNLHGVVGRTSGQAQGFSYTDANK
Pichia guilliermondii   MPAPYEKGSEKKGATLFKTRCLQCHTVEEGAPNKVGPNLHGLIGRKSGQVEGYSYTDANK
Debryomyces occidentalis MPAPYEKGSEKKDANLFKTRCLQCHTVEKGGPHKVGPNLHGIFGRKSGQAAGYSYTDANK
Pichia stipitis         MPAPFEKGSEKKGATLFKTRCLQCHTVEKGGPHKVGPNLHGIMCRKSGQAVGYSYTDANK
Candida albicans        MPAPFEKGSEKKGATLFKTRCLQCHTVEKGGPHKVGPNLHGVFGRKSGLAEGYSYTDANK
Kluyveromyces lactis    MPAPYKKGSEKKGATLFKTRCLQCHTVEAGGPHKVGPNLHGVFGRHSGKASGYSYTDANI
Pachysolen tannophilus  MPAPYEKGSAKKGATLFKTRCLQCHTTEAGGAHKVGPNLNGVFGRHSGQAEGYSYTDANK
Lodderomyces elongisporus MPAFYEKGSSKKGATLFKTRCLQCHTTEKGGANKVGPNLHGVFGRHSGQAEGYSYTEANK
                        ****:;***  **.*.* ****:******.*  *.,:*****:*:.** **  ,*;***;**
Primary consensus       MPAPYEKGSEKKGATLFKTRCLQCHTVE3GGPHKVGPNLHGVFGRKSGQAEGYSYTDANK 70         80         90        100        110
                        |          |          |          |          '
Pichia pastoris         RKGVEWSEQTMSDYLENPKKYIPGTKMAFGGLKKAKDRNDLITYLAKAT(SEQ ID NO: 2)
Debaryomyces hansenii   KKGVEWSEQNLSDYLENPKKYIPGTKMAFGGLKKAKDRNDLISYLVKAT(SEQ ID NO: 5)
Pichia guilliermondii   KKGVEWTEQNLSDYLENPKKYIPGTKMAFGGLKKAKDRNDLITYLVSAT(SEQ ID NO: 7)
Debryomyces occidentalis KKGVEWTEQTMSDYLENPKKYIPGTKMAFGGLKKPKDRNDLITYLANAT(SEQ ID NO: 6)
Pichia stipitis         KKGVEWSEQTMSDYLENPKKYIPGTKMAFGGLKKPKDRNDLVTYLASAT(SEQ ID NO: 8)
Candida albicans        RKGVEWTEQTMSDYLENPKKYIPGTKMAFGGLKKPKDRNDLVTYLKKAT(SEQ ID NO: 9)
Kluyveromyces lactis    KKNVLWDEQTMSDYLENPKKYIPGTKMAFGGLKKEKDRNDIVTYMLKAQ(SEQ ID NO: 10)
Pachysolen tannophilus  QRGALWEAQTMSDYLENPKKYIPGTKMAFGGLKKAKDRNDLVTYLLSAT(SEQ ID NO: 11)
Lodderomyces elongisporus KAGVLWDEQHMSDYLENPKKYIPGTKMAFAGLKKAKDRNDLVTYLKEAT(SEQ ID NO: 12)
                        :  .. *   *  ;************,**** *****:;:*; ,* .
Primary consensus       KKGVEW2EQTMSDYLENPKKYIPGTKMAFGGLKKAKDRNDLVTYLAKATK
```

```
                          10        20        30        40        50        60
                          |         |         |         |         |         |
S. cerevisiae Cyc1p   ----MTEFKAGSAKKGATLFKTRCLQCHTVEKGGPHKVGPNLHGIFGRHSGQAEGYSYTD
S. cerevisiae Cyc7p   MAKESTGFKPGSAKKGATLFKTRCQQCHTIEEGGPNKVGPNLHGIFGRHSGQVKGYSYTD
                       * **.**************** ****:*:***:**************** .:******
Prim.cons.            MAKE2T2FK2GSAKKGATLFKTRC2QCHT2E2GGP2KVGPNLHGIFGRHSGQ22GYSYTD 70        80        90        100       110
                          |         |         |         |         |
S. cerevisiae Cyc1p   ANIKKNVLWDENNMSEYLTNPKKYIPGTKMAFGGLKKEKDRNDLITYLKKACE (SEQ ID NO: 17)
S. cerevisiae Cyc7p   ANINKNVKWDEDSMSEYLTNPKKYIPGTKMAFAGLKKEKDRNDLITYMTKAAK (SEQ ID NO: 18)
                      ***:*** ***:.*******************.*************:.**.:
Prim.cons.            ANI2KNV2WDE22MSEYLTNPKKYIPGTKMAF2GLKKEKDRNDLITY22KA22 (SEQ ID NO: 19)
```

\* denotes amino acid residues that are identical in all the cytochromes c.

: denotes conserved amino acid substitutions.

. denotes semi-conserved amino acid substitutions.

US 7,892,792 B2

CELLS EXPRESSING *PICHIA* CYTOCHROME C

RELATED APPLICATION

This application claims priority to Indian Priority Application 1123/KOL/2008, filed Jun. 27, 2008, including the specification, drawings, claims and abstract, which are incorporated herein by reference in their entireties.

BACKGROUND

*Saccharomyces cerevisiae* (*S. cerevisiae*) is a yeast that has long been used as an expression system for producing exogenous proteins. *S. cerevisiae* and other yeast expression systems, however, are limited, for example, by growth rate and the production of molecules that promote or accelerate particular biochemical pathways.

SUMMARY

One aspect disclosed herein is a recombinant yeast cell comprising a gene encoding a *Pichia* cytochrome C polypeptide although as explained below, the present technology is not limited to the expression of only *Pichia* cytochrome C. In one embodiment, the gene encoding the *Pichia* cytochrome C polypeptide is operably linked to at least one gene regulatory element in a gene expression cassette. In another embodiment, the gene encoding the *Pichia* cytochrome C polypeptide is encoded by an extrachromosomal self-replicating vector. In a further embodiment, the gene encoding the *Pichia* cytochrome C polypeptide is expressed constitutively. Thus, an embodiment is a recombinant yeast cell that expresses a *P. pastoris* cytochrome C polypeptide. In one embodiment, the recombinant yeast cell is a *Saccharomyces cerevisiae* yeast cell.

In another embodiment, the gene encoding the cytochrome C polypeptide comprises a nucleic acid of SEQ ID NO:1 or a functional fragment thereof. In a further embodiment, the cytochrome C polypeptide encoded by the gene comprises an amino acid sequence of SEQ ID NO:2 or is a homolog with at least about 85% sequence identity to the cytochrome C polypeptide encoded by the gene has an amino acid sequence of SEQ ID NO:2. In another embodiment a cytochrome C homolog shares about 85%, 86%, 87%, 88%, 89%, 90%, 91%, 92%, 93%, 94%, 95%, 96%, 97%, 98%, or 99% sequence identity with the amino acid sequence of SEQ ID NO:2.

In another embodiment, the recombinant cell further comprises a recombinant gene cassette that expresses a target gene. In one embodiment, the target gene is integrated into the cell genome or expressed extrachromosomally in a self-replicating plasmid. In a further embodiment, the target gene is selected from the group of hepatitis B surface antigen gene, insulin genes, erythropoietin genes, interleukins (e.g., IL-2, IL-4, IL-6, IL-10, IL-11, IL-15), growth hormones, calcitonins, tpA, streptokinases, bacterial toxins, dengue virus antigens, TGF-beta-1, VEGF, VEGF-165, G-CSF, M-CSF and TNF-alpha.

In a farther embodiment, the yeast cell does not express an endogenous gene that encodes a biologically active cytochrome C polypeptide. That is, in one embodiment, the yeast cell does not express a native, endogenous cytochlome C gene (see FIG. 9).

In another aspect is a recombinant *S. cerevisiae* cell comprising a polynucleotide of SEQ ID NO:1. In one embodiment, the *S. cerevisiae* cell does not express an endogenous gene encoding a biologically active cytochrome C polypeptide.

In one embodiment, the recombinant *S. cerevisiae* cell further comprises a recombinant gene cassette that expresses a target gene. In one embodiment, the target gene is integrated into the cell genome. In another embodiment, the target gene is a hepatitis B surface antigen gene, an insulin gene or an erythropoietin gene.

Another aspect is a method for increasing the growth potential of a yeast cell, comprising recombinantly engineering the yeast cell to comprise a gene encoding a cytochrome C polypeptide, thereby increasing the growth potential of the yeast cell. In one embodiment, the gene encodes a *Pichia* cytochrome C polypeptide. In one embodiment, the growth rate of the recombinant yeast cell is faster after about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours or more than about 24 hours, of culture than the growth rate of a wild-type yeast cell. In one embodiment, the growth rate of the recombinant yeast cell is faster after about 1-2 hours, after about 2-5 hours, after about 5-10 hours, or after about 12-16 hours of culture than the growth rate of a wild-type yeast cell. In one embodiment, the growth rate of the recombinant yeast cell is faster than that of the wild-type yeast cell after about 12-16 hours. In one embodiment, a faster rate of growth of the recombinant yeast cell is observed within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours or within about 20 hours after being grown on glucose medium. In this regard, any of the recombinant yeast cells disclosed herein can be used in the methods described herein.

Another aspect is a method for enhancing the production of polyunsaturated fatty acid precursor molecules in a recombinant yeast cell, comprising growing a recombinant yeast cell that expresses a *P. pastoris* cytochrome C polypeptide on an oleic acid substrate under conditions wherein the recombinant yeast cell accumulates more intracellular oleic acid than a wild-type yeast cell. In one embodiment, the method further comprises growing the recombinant yeast cell on a glucose-containing substrate for at least about 1 hour, about 2 hours, about 3 hours, about 4 hours, about 5 hours, about 6 hours, about 7 hours, about 8 hours, about 9 hours, about 10 hours, about 11 hours or about 12 hours prior to growing the cells on the oleic acid substrate. In a further embodiment, the recombinant yeast cell does not comprise an endogenous gene encoding a biologically active cytochrome C polypeptide.

Another aspect is a method for producing a polyunsaturated fatty acid molecule in a recombinant yeast cell that expresses a *P. pastoris* cytochrome C polypeptide and further comprises at least one gene encoding a polypeptide selected from the group consisting of $\Delta$6-desaturase, elongase, $\Delta$12-desaturase, $\omega$3-desaturase and $\Delta$5-desaturase, by culturing the recombinant yeast cell under conditions wherein a polyunsaturated fatty acid is produced. In one embodiment, the polyunsaturated fatty acid is selected from the group consisting of: linoleic acid, linolenic acid, omega-3 fatty acid and omega-6 fatty acid.

Another aspect is a method for producing polyunsaturated fatty acids, comprising (A) extracting intracellular oleic acid from the recombinant yeast cell that expresses a *P. pastoris* cytochrome C polypeptide, which is either grown on an oleic acid substrate or grown on a glucose substrate for at least about 5-12 hours before being grown on an oleic acid substrate; and either (B) chemically or enzymatically converting the extracted oleic acid in vitro into at least one polyunsaturated acid; or (C) feeding the extracted oleic acid to a cell that naturally converts the internalized oleic acid to at least one polyunsaturated acid, or that has been engineered to convert the internalized oleic acid to at least one polyunsaturated acid.

Another aspect is a method of producing an isolated target polypeptide comprising (A) culturing any one of the recombinant yeast cells that expresses a *P. pastoris* cytochrome C gene disclosed herein under conditions wherein the yeast cell expresses the target gene, and (B) isolating the polypeptide product of the expressed target gene, thereby producing an isolated target polypeptide. In one embodiment, the recombinant yeast cell is cultured on a glucose-containing substrate for more than about 12 hours. In a further embodiment, the target gene comprises a polynucleotide sequence that encodes a signal or secretion peptide, wherein the expressed polypeptide product is transported out of or secreted from the recombinant yeast cell. In one embodiment, the step (B) of isolating the polypeptide product of the expressed target gene comprises centrifuging an aliquot of the yeast cell culture and then purifying the polypeptide product from the culture supernatant.

As mentioned above, the present technology is not limited to the expression of only a *P. pastoris* cytochrome C gene in a yeast cell. Genes encoding cytochrome C polypeptides from other organisms can be similarly used according to the compositions and methods disclosed herein. For instance, a cytochrome C gene from any of the following fungal genera can be expressed in a yeast cell: *Debaryomyces hansenii*, *Debryomyces occidentalis*, *Pichia guilliermondii*, *Pichia stipitis*, *Candida albicans*, *Kluyveromyces lactis*, *Pachysolen tannophilus* and *Lodderomyces elongisporus*. Examples of amino acid sequences for other cytochrome C sequences are shown in FIG. 8.

Furthermore, accordingly, any cytochrome C or a variant that conforms with the amino acid consensus sequence depicted in SEQ ID NO:4 can be expressed according to the present methods in yeast cells. Accordingly, embodiments of the present technology that expressly recite the expression of a *P. pastoris* cytochrome C gene or polypeptide are not limited to the expression of that particular cytochrome C from that particular yeast species. The recitation of the *P. pastoris* cytochrome C gene or polypeptide is primarily for ease of communicating the concepts, compositions and methods.

BRIEF DESCRIPTION OF THE DRAWINGS

FIG. 7 is a sequence alignment of cytochrome C amino acid sequences from *S. cerevisiae* (SEQ ID NO:3) and *P. pastoris* (SEQ ID NO:2).

FIG. 8 is a sequence alignment of cytochrome C amino acid sequences from different fungal species (A) and different *S. cerevisiae* sequences (SEQ ID NOS:2, 5, 7, 6, 8-12 and 4, in order), (B) The CXXCH motif (underlined text, SEQ ID NO:20), conserved in all cytochrome C polypeptide sequences, is underlined (SEQ ID NOS:17-19).

DETAILED DESCRIPTION

Figure 1:
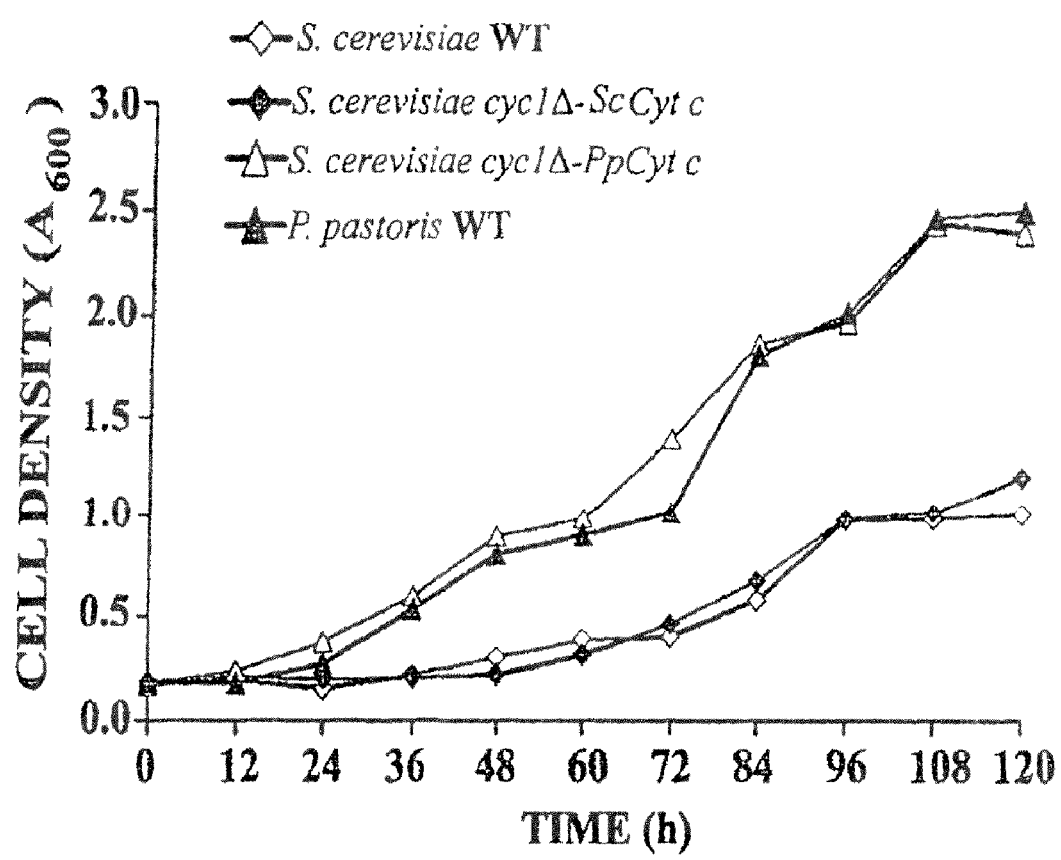
FIG. 1 is a series of growth curves for different yeast strains grown in YNBO medium containing oleic acid as the sole carbon source. The growth rate of *S. cerevisiae* cyc1Δ-PpCyt C cells was higher than that of *S. cerevisiae* cyc1Δ-ScCyt C when these cells are grown in YNBD medium containing glucose as the sole carbon source (see FIG. 2).

Described herein are methods, materials and compositions for the creation of recombinant yeast cells that (i) grow faster than the wild-type yeast cells of the same species when cultured on glucose medium, as well as (ii) accumulate high levels of polyunsaturated fatty acid precursor molecules when grown on oleic acid. Methods and kits for using these recombinant yeast cells are also described. The two features of the recombinant yeast cells permit several different applications that include large-scale production of desired polypeptides and polyunsaturated fatty acids. Accordingly, aspects of the technology include but are not limited to: any recombinant yeast cell that expresses any yeast cytochrome C gene; any recombinant yeast cell that expresses any yeast cytochrome C gene that has a faster rate of growth than the wild type yeast cell when grown on glucose, any recombinant yeast cell that expresses any yeast cytochrome C gene and any desired gene, where the yield of the desired gene product per unit time is greater than the yield of that desired gene product from the wild type yeast cell of the same species; any recombinant yeast cell that expresses any yeast cytochrome C gene that accumulates greater levels of intracellular oleic acid than the wild type yeast cell of the same species when grown on oleic acid (The oleic acid can be extracted from these cells and either fed to a cell type that can naturally convert the oleic acid into polyunsaturated fatty acids and its intermediaries, or converted chemically and enzymatically into a polyunsaturated fatty acid.); and any recombinant yeast cell that expresses any yeast cytochrome C gene that is grown on oleic acid and expresses at least one other gene that promotes the conversion of polyunsaturated fatty acid precursor molecules into polyunsaturated fatty acids.

Embodiments include, but are not limited to: recombinant yeast cells, e.g., S. cerevisiae, that expresses a cytochrome C gene, wherein the cytochrome C gene can be the P. pastoris cytochrome C gene; recombinant yeast cells that express a yeast cytochrome C gene, e,g., the P. pastoris cytochrome C gene, and have a faster rate of growth than wild type yeast cells when grown on glucose; recombinant yeast cells that express the P. pastoris cytochrome C gene and a desired gene, wherein the yield of the desired gene product per unit time is greater than the yield of that desired gene product from the wild type yeast cell of the same species; recombinant yeast cells that express the P. pastoris cytochrome C gene that accumulate greater levels of intracellular oleic acid than wild type yeast cells of the same species when grown on oleic acid (The oleic acid can be extracted from these cells and either fed to a cell type that can naturally convert the oleic acid into polyunsaturated fatty acids and its intermediaries, or converted chemically and enzymatically into a polyunsaturated fatty acid.); and recombinant yeast cells that express a yeast cytochrome c gene, e.g., P. pastoris cytochrome C gene and are grown on oleic acid to express at least one other gene that promotes the conversion of polyunsaturated fatty acid precursor molecules into polyunsaturated fatty acids.

The recombinant host yeast cells that express the cytochrome C gene are not limited to S. cerevisiae, and the cytochrome C gene is not limited to the P. pastoris cytochrome C gene.

Cytochrome C Genes and Homologs

Cytochrome C is an ubiquitous electron transport protein that is normally localized in mitochondria and is involved functionally in aerobic and anaerobic respiration as well as other cellular processes like apoptosis and photosynthesis. It is an essential component of the electron transfer chain in which it carries one electron and is capable of undergoing oxidation and reduction but does not bind oxygen. Cytochrome C transfers electrons between Complexes III and IV of the electron transport pathway and also functions to catalyze several reactions such as hydroxylation and aromatic oxidation. It also exhibits functional peroxidase activity by oxidation of various electron donors such as 2,2-azino-bis(3-ethylbenzthiazoline-6-sulphonic acid) (ABTS), 2-keto-4-thiomethyl butyric acid and 4-aminoantipyrine.

One useful cytochrome C gene is the P. pastoris cytochrome c gene sequence. The DNA sequence of the P. pastoris cytochrome C sequence is shown in SEQ ID NO:1 and the corresponding amino acid sequence is shown in SEQ ID NO:2. Cytochrome C genes typically differ from other cytochrome genes because they having a covalent ligation of bound heme vinyl groups to the cysteine residues of apocytochrome c in a "CXXCH" amino acid motif (SEQ ID NO:20; see FIG. 8). The CXXCH (SEQ ID NO:20) motif is required for heme binding and for cytochrome C function. Amino acids in the N-terminal region of cytochrome C are required for its import into mitochondria. The N- and C-terminal amino acids contribute to stability of the protein (Sherman, F. et al., Genetics, 77: 255-284, 1974; Dumont, M. et al., J. Biol. Chem., 263:15928-15937, 1988). In one embodiment, a functional cytochrome C fragment is one that comprises the CXXCH motif (SEQ ID NO:20; FIG. 8 (underlined sequences)).

Variants of the P. pastoris cytochrome C gene and polypeptide product can be used. A variant, as used herein, is understood to mean a nucleotide or amino acid sequence that deviates from a standard nucleotide or amino acid sequence of a particular gene or protein. The terms "isoform," "isotype," and "analog" also refer to "variant" forms of a nucleotide or an amino acid sequence. An amino acid sequence that is altered by the addition, removal or substitution of one or more amino acids, or a change in nucleotide sequence, can be considered a "variant" sequence. The variant can have "conservative" changes, wherein a substituted amino acid has similar structural or chemical properties, e.g. replacement of leucine with isoleucine. A variant can have "nonconservative" changes, e.g, replacement of a glycine with a tryptophan. Analogous minor variations can also include amino acid deletions or insertions, or both. Guidance in determining which amino acid residues can be substituted, inserted, or deleted can be found using computer programs such as, for example, Vector NTI Suite (InforMax, MD) software. A variant cytochrome C gene or polypeptide product described herein therefore also includes mutants of cytochrome C. That is, a cytochrome C can be mutated to increase or decrease its functionality or ability to transfer electrons, bind heme, or interact with other proteins in the cytochrome respiration pathway.

Methods described herein are not limited to the expression of only SEQ ID NO:1 in a yeast cell to produce the SEQ ID NO:2 polypeptide. Other functional variants or fragments of the P. pastoris cytochrome C gene can be expressed in a recombinant yeast cell The method encompasses, for example, the expression of a polynucleotide that shares at least about 99%, 98%, 97%, 96%, 95%, 94%, 93%,92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% sequence identity with SEQ ID NO:1. Alternatively, any polynucleotide that encodes the full-length polypeptide sequence of SEQ ID NO:2 can be expressed in a recombinant yeast cell. The methods also encompass the expression of a functional polypeptide product that shares at least about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% sequence identity with SEQ ID NO:2.

Other fungal or yeast cytochrome C genes, not only the P. pastoris gene, can be expressed in a recombinant yeast cell. The methods herein, for example, encompass the expression of Debaryomyces hansenii cytochrome C, Debaryomyces occidentalis cytochrome C, Pichia guilliermondii cytochrome C, Pichia stipitis cytochrome C, Candida albicans cytochrome C, *Kluyveromyces lactis* cytochrome C, *Pachysolen tannophilus* cytochrome C, and *Lodderomyces elongisporus* cytochrome C in a recombinant yeast cell. An example of *D. hansenii* cytochrome C polypeptide sequence is shown in SEQ ID NO:5. An example of *D. occidentalis* cytochrome C polypeptide sequence is shown in SEQ ID NO:6. An example of *P. guilliermondii* cytochrome C polypeptide sequence is shown in SEQ ID NO:7. An example of *P. stipitis* cytochrome C polypeptide sequence is shown in SEQ ID NO:8. An example of *C. albicans* cytochrome C polypeptide sequence is shown in SEQ ID NO:9. An example of *K. lactis* cytochrome C polypeptide sequence is shown in SEQ ID NO:10. An example of *P. tannophilus* cytochrome C polypeptide sequence is shown in SEQ ID NO:11. An example of *L. elongisporus* cytochrome C polypeptide sequence is shown in SEQ ID NO:12. Any one of these cytochrome C polypeptides or functional variants can be expressed in a recombinant yeast cell by an appropriate polynucleotide sequence or variant thereof.

As used herein, "sequence identity" or "identity" in the context of two nucleic acid or polypeptide sequences includes reference to the residues in the two sequences that are the same when aligned for maximum correspondence over a specified region. Where percentage of sequence identity is used in reference to proteins it is recognized that residue positions that are not identical often differ by conservative amino acid substitutions, where amino acid residues are substituted for other amino acid residues with similar chemical properties (e.g., charge or hydrophobicity) and therefore do not change or minimally change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are known to those of skill in the art. This typically involves scoring a conservative substitution as a partial rather than a full mismatch, thereby increasing the percentage sequence identity. Thus, for example, where an identical amino acid is given a score of 1 and a non conservative substitution is given a score of 0, a conservative substitution is given a score between 0 and 1. The scoring of conservative substitutions is calculated, e.g., according to the algorithm of Meyers and Miller (*Computer Applic. Biol. Sci.*, 4:11-17, 1988), as implemented, for example, in the program PC/GENE (Intelligenetics, Mountain View, Calif., USA).

As used herein, "percentage of sequence identity" or "percent sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Methods of aligning sequences for comparison are known in the art. Optimal alignment of sequences for comparison may be conducted by the local homology algorithm of Smith and Waterman (*Adv. Appl. Math.*, 2:482, 1981); by the homology alignment algorithm of Needleman and Wunsch (*J. Mol. Biol.*, 48:443, 1970); by the search for similarity method of Pearson and Lipman (*Proc. Natl. Acad. Sci. USA*, 85:2444, 1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCC), 575 Science Dr., Madison, Wis., USA. The CLUSTAL program is described by Higgins and Sharp (*Gene*, 73:237-244, 1988); Higgins and Sharp (*CABIOS*, 5:151-153, 1989); Corpet et al. (*Biosciences*, 8:155-65, 1992); and Pearson, W. (*Methods Mol. Biol.*, 24:307-331, 1994).

The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences (see Current Protocols in Molecular Biology, Chapter 19, Ausubel, et al, Eds., Greene Publishing and Wiley-Interscience, New York (1995); Altschul et al, *J. Mol Biol.*, 215:403-410, 1990; and, Altschul et al., *Nucleic Acids Res.*, 25:3389-3402, 1997).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA*, 89:10915, 1989).

In addition to calculating percent sequence identity, the BLAST algorithm also performs a statistical analysis of the similarity between two sequences (Karlin and Altschul, *Proc. Natl. Acad. Sci. USA*, 90:5873-5877, 1993). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. Many real proteins, however, comprise regions of nonrandom sequences that may be homopolymeric tracts, short-period repeats, or regions enriched in one or more amino acids. Such low-complexity regions can be aligned between unrelated proteins even though other regions of the protein are entirely dissimilar. A number of low-complexity filter programs can be employed to reduce such low-complexity alignments. The SEG (Wooten and Federhen, *Comput. Chem.*, 17:149-163, 1993) and XNU (Claverie and States, *Comput. Chem.*, 17:191-201, 1993) low-complexity filters, for example, can be employed alone or in combination.

Multiple alignment of the sequences can be performed using the CLUSTAL method of alignment with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

A gene or polynucleotide encoding a functional yeast cytochrome C polypeptide is operably linked to at least one regulatory element that facilitates the expression of the gene or polynucleotide and the corresponding polypeptide product in a yeast cell. A regulatory element is a sequence that is standard and known to those in the art, that may be included in the expression vectors to increase and/or maximize transcription of a gene of interest or translation of the resulting RNA in a plant system These include, but are not limited to, promoters, enhancer elements, peptide export signal sequences, introns, polyadenylation, and transcription termination sites. The expression vectors can have a transcription termination region at the opposite end from the transcription initiation regulatory region. The transcription termination region can be selected, for example, for stability of the mRNA to enhance expression and/or for the addition of polyadenylation tails added to the gene transcription product (Alber and Kawasaki, *Mol. Appl. Genetics*, 4:19-34, 1982). Illustrative transcription termination regions include, for example, the E9 sequence of the pea RBCS gene (Mogen et al., *Mol. Cell Biol.*, 12:5406-14, 1992) and the termination signals of various ubiquitin genes.

Methods of modifying nucleic acid constructs to increase expression levels in yeast cells are also generally known in the art In engineering a yeast cell to affect the rate of transcription of a protein, various factors known in the art, including regulatory sequences such as positively or negatively acting sequences, enhancers and silencers, as well as chromatin structure may have an impact. Thus, a cytochrome C gene or polynucleotide can be operably linked to one or more of these elements, such as, for example, to a promoter that is functional in a yeast cell and a terminator. An example of a promoter that is functional in yeast cells includes the TEF2 promoter. Other promoters that are functional in yeast cells include those provided in the database described by Zhu and Zhang (*Bioinformatics*, 15:607-11, 1999) as well as alcohol dehydrogenase (ADH1), phosphoglycerate kinase (PGK1), enolase (ENO), pyruvate kinase (PYK1), galactose metabolic enzymes (GAL1,10,7), alcohol dehydrogenase 2 (ADH2), acid phosphotase (PHO5), O-acetyl homoserine sulphydrylase (MET25), copper metallothionein (CUP1), cauliflower mosaic virus 35S promoter (CaMV), glucocorticoid response element (GRE), and androgen response element (ARE), Glyceraldehyde-3-phosphate dehydrogenase (GAP). The regulatory elements such as, for example, the promoter, can be inducible or constitutive. The expression of the cytochrome C gene can either be switched on and off, for example in response to certain ingredients or chemicals in the culture medium, or expressed constitutively at all times regardless of the culture substrate. The resultant expression cassette can be subcloned into an appropriate plasmid or vector construct Vector Design A vector can be used to introduce a cytochrome C expression cassette into a desired yeast cell to produce a recombinant yeast cell. In addition to the cytochrome C expression cassette, the vector can have one or more selectable markers to help identify transformants. Furthermore, the vector can have genetic elements that help excise and integrate the expression cassette from the vector backbone and into the target yeast cell genome. The vector can have, for example, sequences that promote homologous recombination with a region of the yeast cell genome into which region the cytochrome C gene becomes integrated. In such a situation, the expression cassette becomes a stable component of the yeast cell genome and is propagated throughout successive cell divisions and generations. Accordingly, the integrated cytochrome C gene product is present in progeny cells The vector optionally can be a self-replicating vector that does not recombine with the host cell genome but instead exists independently, i.e., extrachromosomally, within the cell from which the cytochrome C gene is expressed Vectors useful for expression of polypeptides in yeast include, but are not limited to, integrative plasmids (YIp), episomal plasmids (YEp), autonomously replicating plasmids (YRp), epitope-tagged vectors (pESC), and Cen plasmids (YCp).

The vector can have an additional expression cassette that expresses a desired gene.

Types of Host Yeast Cells for Expressing Cytochrome C Genes

Any yeast cell can be transformed to express one or more of the cytochrome C genes. Examples of yeast cells include, but are not limited to, *S. cerevisiae, D. hansenii, D. occidentalis, P. guiliermondii, P. stipitis, P. pastoris, P. methanolica, C. albicans, K. lactic, P. tannophilus, L. elongisporus, S. pombe, Y. lipolytica,* and *H. polymorpha.* Any such yeast cells can be engineered to express a cytochrome C from either the same or different yeast species. Furthermore, the host yeast cell can have one or more of its own endogenous cytochrome C genes disrupted or knocked-out to prevent expression of its native cytochrome C protein. Accordingly, the methods encompass the expression of a cytochrome C gene sequence in a null or partially null genetic background for native cytochirome C expression. The skilled artisan knows how to knock-out, downregulate or otherwise silence the expression of an endogenous, i.e., native, yeast cell cytochrome C gene by implementing standard laboratory procedures. Silencing the expression of endogenous yeast genes can be accomplished, for example, by a gene disruption procedure involving the use of a linear fragment of DNA containing a selectable marker (e.g., URA3, LEU2, ADE1 etc.) flanked by 5' and 3' homologous regions of the gene of interest. The free ends of the fragment, prepared by digestion with restriction endonucleases, are recombinogenic, resulting in the integration of URA3 marker and the loss of wild type allele of the gene of interest.

A "recombinant yeast cell" as described herein therefore is one that at least expresses one or more cytochrome c genes and includes yeast cells in which the endogenous, native cytochrome c genes have been knocked out. It also includes yeast cells that express a cytochrome c gene and some other gene from another expression cassette, such as a desired gene or a pathway gene as discussed below.

Deposits of biological materials associated with the recombinant yeast strains described herein were made with the International Depositary Authority (IDA), Microbial Type Culture Collection and Gene Bank (MTCC), Institute of Microbial Technology (IMTECH), Chandigarh, INDIA. Specifically, a *S. cerevisiae* strain expressing *P. pastoris* cytochrome C gene termed, *S. cerevisiae* cyc1Δ-PpCytc, was deposited on Jun. 9, 2008 as described above and assigned accession number MTCC5429.

Permutations of Yeast Cells and Cytochrome C Genes

Described herein are methods and compositions for the expression of *P. pastoris* cytochrome C in a *S. cerevisiae* yeast cell. The *S. cerevisiae* yeast cell may or may not express one or all of its endogenous cytochrome C genes (cyc1, cyc7). The cyc1 and cyc7 genes contribute to 95% and 5% of the total cytochrome C content of *S. cerevisiae* cells respectively. Thus, the *S. cerevisiae* genome can be engineered to prevent expression of its cytochrome C gene sequences so that the only or the major cytochrome C polypeptide in the *S. cerevisiae* cell is the *P. pastoris* cytochrome C. The skilled artisan recognizes that in genetic nomenclature the *S. cerevisiae* strain lacking the cyc1 gene (cyc1Δ) engineered to express *P. pastoris* cytochrome C, may be denoted, as described herein, as *S. cerevisiae* cyc1Δ-PpCytc.

Alternatively, the expression of native *S. cerevisiae* cytochrome C genes can remain intact so that both the endogenous *S. cerevisiae* cytochrome C polypeptides and the *P. pastoris* cytochrome C polypeptides are present in that recombinant yeast cell. Furthermore, the present methods encompass the expression of multiple *P. pastoris* cytochrome C genes. Two or more copies, for example, of a *P. pastoris* cytochrome C gene or variant can be subcloned into the same or different transformation vector(s) so that the host *S. cerevisiae* cell expresses multiple copies of the *P. pastoris* cytochrome C polypeptide. Any of these gene/cell permutations can be applied to other host yeast cells and to the expression of cytochrome C genes from species other than *P. pastoris*. In one embodiment, the cytochrome C gene that is expressed in the host yeast cell is from a species that is different from the host yeast cell, e.g., *P. pastoris* cytochrome C in *S. cerevisiae* cells.

Transformation

A yeast cell can be transformed according to various standard molecular biology protocols, including but not limited to standard heat shock transformation procedures or electroporation (see, for example, Hinnen et al., *Proc, Natl. Acad. Sci. USA*, 75:1929-1933, 1978). A culture of yeast is typically grown for a period of time on a desired media or liquid media, such as overnight, to a particular cell density. This can be accomplished, for example, by manually counting the cells using a haemocytometer grid under microscope visualization. *S. cerevisiae* cells divide by budding from a mother cell and the budded cells can be counted as a single cells. Those cells can then be cultured and then pelleted. A transformation mix, which includes the vector construct, can be added to the pellet. The cell/transformation mix can then be vortexed until the pellet is resuspended and then placed in a hot water bath for heat shock, e.g., at 42° C. for a period of time, such as 5-40 minutes. The heat shock process creates re-closable pores in the yeast cell membrane through which the vector passes into the cell. Afterwards, the cells can be plated onto appropriate substrate and left to grow overnight, whereafter they can be evaluated to determine whether they express the introduced vector's expression cassette.

Alternatively, a suspension of yeast cells can be exposed to a vector transformation mix and then pulsed with an electroporator charge, such as, for example, one pulse of 1.5 kV, 25 μF, 200 Ohms, for a few minutes.

Another method of transformation of yeast cells involves treatment of yeast cells with lithium acetate as described at the website, fhcrc.org/science/labs/gottschling/yeast/ytrans.html.

Media for Faster Growth Rate

Recombinant yeast cells can be grown on a variety of media. In the case of *S. cerevisiae* cells that express *P. pastoris* cytochrome C, desirable media that contains glucose (YNBD) as the sole carbon source or oleic acid (YNBO) as the sole carbon source. Recombinant *S. cerevisiae* cells can be cultured and maintained on YNBD medium that contains 0.67% (w/v) yeast nitrogen base (YNB) without amino acids, amino acids as required, and 2% (w/v) glucose. When yeast cells are to be cultured on oleic acid, cells are first cultured overnight in YNBD medium and then transferred to YNBO medium (YNB+0.5% oleic acid+0.05% Tween 40) and grown further for different time periods. In some experiments, oleic acid can be replaced by stearic acid (YNBS). For growth assays in liquid oleic acid medium, cells are grown overnight in YNBD medium and the cultures were diluted to an A600 of 0.1 in a medium containing YNB, 0.5% oleic acid emulsified with 0.05% Tween 40 (YNBO). YNBO cultures are then washed free of medium, resuspended in water and $A_{600}$ measured at various time points. All the yeast strains can be grown in shaker flasks or in test tubes at 30° C. or in any vessel that is desirable for large-scale production. For oleic acid uptake studies, cells are cultured in presence of 1.0 μCi/mL [1-$^{14}$C]oleic acid (3.7 MBq/mL, PerkinElmer) and the concentration of unlabelled oleic acid and Tween 40 in the medium was reduced to 0.05% (v/v) and 0.005% (v/v), respectively.

*S. cerevisiae* cells that express *P. pastoris* cytochrome C were unexpectedly observed to have increased growth potential on glucose medium than wild type *S. cerevisiae* cells grown on glucose.

A second surprising discovery is that *S. cerevisiae* cells that express the *P. pastoris* cytochrome C, accumulate much higher intracellular levels of oleic acid when grown on a medium containing oleic acid or glucose than wild type *S. cerevisiae* cells grown on oleic acid or glucose medium.

Expressing a Desired Gene in the Recombinant Yeast Host Cell

The materials and methods described herein encompass expressing a desired gene in a recombinant yeast cell that expresses one or more cytochrome C genes. A recombinant yeast cell line can be transformed, for example, to contain an extrachromosomal vector that expresses a desired gene or transformed such that the expression cassette that expresses the desired gene is integrated into the cell genome. Thus, another aspect is a recombinant yeast cell that expresses (1) at least one cytochrome C gene and (2) a desired gene.

Thus, the present technology encompasses the growth of a recombinant yeast cell on, for instance glucose medium, wherein the yeast cell grows faster than the wild type counterpart when it expresses the *P. pastoris* cytochrome C gene;

and the subsequent or concomitant expression of the desired gene. Because the recombinant yeast cells divide and bud faster than the wild type, that suspension reaches a greater biomass in shorter period of time, and therefore the production and accumulation of the desired gene product will be greater than it would be if expressed in wild type yeast cell.

Accordingly, the present technology encompasses the increased yield of a desired gene product by expressing the gene or polynucleotide that encodes that product in a recombinant yeast cell line. Examples of genes for include but are not limited to a hepatitis B surface antigen gene, an insulin gene, and an erythropoietin gene.

Any desired protein or polypeptide product can be expressed, produced, and subsequently isolated at higher levels than would be possible using conventional, non-engineered wild type yeast cells. Accordingly, the present methods encompass yields of a desired product at levels that are at least about 2-fold, 5-fold, 10-fold, 15-fold, 20-fold, or more than 20-fold the level of wild type yields for the same protein product when it is expressed in a recombinant yeast cell. The present methods encompass yields of a desired product at levels that are at least about 2- to 5-fold, 5- to 10-fold, 10- to 15-fold, 15- to 20-fold, 20- to 30-fold, or more than 30-fold the level of wild type yields for the same protein product when it is expressed in a recombinant yeast cell. Thus, the present methods conveniently and cost-effectively permit the large-scale, commercial production of a desired gene product. Furthermore, large-scale yeast production through fermentative methods and other down stream processes for yeast is simple, safe and well characterized. Yeast is generally considered as a safe organism and owing to their rapid high cell density growth, allowing for the global demands of ω-3 fatty acids (eicosapentaenoic acid or docosahexaenoic acid or DHA) and ω-6 fatty acids (gamma-linolenic acid or GLA, dihomo-gamma-linolenic acid or DGLA and arachidonic acid or AA) to be met using the described recombinant yeast cells and methodologies ω-3 and ω-6 fatty acids that are synthesized from α-Linolenic acid (18:3) and Linoleic acid (18:2), respectively, by a number of organisms other than humans offer several health benefits. DHA, for example, is a major fatty acid in sperm and brain phospholipids, and especially in the retina. Dietary DHA reduces the risk of heart disease by reducing the level of blood triglycerides in humans. Low levels of DHA result in reduction of brain serotonin levels and have been associated with ADHD, Alzheimer's disease, and depression, among other diseases, and there is mounting evidence that DHA supplementation may be effective in combating such diseases.

In addition to large-scale production of a particular desirable gene product, the present methods also encompass the expression of one or more genes that are useful in promoting, regulating, or de-regulating any of the recombinant host yeast cell's biological or biochemical pathways. The purpose for expressing one or more pathway genes is to regulate or enhance an endogenous biological cascade, such as to promote the conversion of certain intermediate molecules into precursor molecules or to create an accumulation of molecules upon which other naturally expressed endogenous proteins and enzymes can act. In this regard, the present technology encompasses the expression of genes involved in the polyunsaturated fatty acid pathway in yeast cells as explained in the following subsection.

Increasing Intracellular Levels of Polyunsaturated Fatty Acid Precursors

Polyunsaturated fatty acids are typically regarded as "healthy fats" that are mostly found in grains, fish, fish oil, and soybeans. Yeast cells can be used to produce polyunsaturated fatty acids. A recombinant yeast cell that expresses a cytochrome C gene, e.g., from *P. pastoris*, can accumulate large intracellular quantities of oleic acid—a polyunsaturated fatty acid precursor—when the recombinant yeast cell is grown on media that contains oleic acid or glucose. The present methods therefore encompass a recombinant yeast cell that accumulates intracellular levels of oleic acid that are at least about 2-fold, 5-fold, 10-fold, 15-fold, 20-fold, or more than 20-fold the level of oleic acid that accumulates in non-recombinant wild type yeast of the same species. Accordingly, the present methods encompass accumulations of oleic acid at levels that are at least about 2- to 5-fold, 5- to 1 0-fold, 10- to 15-fold, 15- to 20-fold, 20- to 30-fold, or more than 30-fold the level of wild type accumulation of oleic acid.

In addition to expressing, for example, a *P. pastoris* cytochrome C gene, the recombinant yeast cell can also express a desaturase or elongase gene that is involved in converting various molecules and polyunsaturated fatty acid precursor molecules into desired polyunsaturated fatty acids. Examples of other such enzymes include but are not limited to Δ6-desaturase, elongase, Δ12-desaturase, ω3-desaturase, and Δ5-desaturase. Examples of desirable long chain polyunsaturated fatty acids that can be produced in this regard include but are not limited to γ-linoleic acid, arachidonic acid and ecosapentaenoic acid.

One skilled in the art will be able to identify various candidate genes encoding Δ12 desaturase and/or Δ6 desaturase activities. The sequences may be derived from any source, e.g., isolated from a natural source (from bacteria, algae, fungi, plants, animals, etc.), produced via a semi-synthetic route or synthesized de novo In some embodiments, manipulation of genes endogenous to the host can be performed in addition to introduction of heterologous genes (see WO 2006/033723, which is incorporated herein by reference in its entirety).

As the skilled artisan is aware, the particular functionalities required to be introduced into a host organism for production of a particular polyunsaturated fatty acid product can depend on several factors, including the type of host cell and the profile of its native polyunsaturated fatty acids and enzymatic, e.g., desaturase and elongase, profile, as well as the availability of substrate, and the desired end product, γ-linolenic acid (GLA), for example, which has been shown to reduce increases in blood pressure associated with stress and to improve performance on arithmetic tests, is produced from oleic acid and linoleic acid. GLA can be produced in yeast by introducing a Δ12 desaturase and a Δ6 desaturase and subsequent polyunsaturated fatty acid derivatives, including di-homo-γ-linoleic acid (DGLA), arachidonic acid (ARA), stearidonic acid (STA), eicosatetracnoic acid (ETA), eicosapentaenoic acid (EPA), docosapentaenoic acid (DPA), and docosahexaenoic acid (DHA), may also be produced if the host possesses endogenous or exogenous Δ4, Δ5, Δ15 and/or Δ17 desaturase activities and/or C18720 and/or C20722 activities.

In vitro methods for converting extracted oleic acid into polyunsaturated fatty acids involve sequential use of recombinant enzymes of the polyunsaturated fatty acid biosynthetic pathway leading to the production of various intermediates of the pathway and the desired polyunsaturated fatty acid. Incubation of the oleic acid, for example, with a recombinant Δ12 desaturase would produce linoleic acid. Conversion of linoleic acid to γ-linolenic acid would require the incubation of linoleic acid with recombinant Δ15 desaturase.

The details of engineering recombinant *S. cerevisiae* cells to express genes that convert oleic acid to polyunsaturated fatty acids are known to the skilled artisan (see, for example, WO/2006/064317 and WO2004104167, which relate to the conversion of oleic acid to linolenic acid; WO2005047480, which relates to the conversion of linolenic acid to α-linoleic acid; and WO2000055330, which describes the method of synthesizing di-homo-gamma-linolenic acid from γ-linolenic acid catalyzed by the polyunsaturated fatty acid elongase enzyme and also the expression of the recombinant polyunsaturated fatty acids elongase of *C. elegans* in yeast; US Publication 2003163845, which describes the use of an elongase gene in combination with the Δ5-desaturase genes in *S. cerevisiae* resulting in the production of arachidonic acid; U.S. Pat. No. 6,432,684, which relates to the identification of a gene involved in the desaturation of polyunsaturated fatty acids and conversion of DGLA to arachidonic acid and in the conversion of 20:4n-3 to EPA; and DE 2003-10335992, which describes the construction of a *S. cerevisiae* host expressing genes from *Euglena gracilis* and *Phaeodactylum tricornutum*; the entire contents of these references is herein incorporated by reference). The organism was able to synthesize docosahexaenoic acid from staeridonic acid or eicosapentaenoic acid, While various aspects and embodiments have been disclosed herein, other aspects and embodiments will be apparent to those skilled in the art. The various aspects and embodiments disclosed herein, and in the following Examples, are for purposes of illustration and are not intended to be limiting, with the true scope and spirit being indicated by the following claims.

EXAMPLES

Example 1

The sources for the vectors and strains are shown in Table 1.

TABLE 1

Yeast strains, plasmids and oligonucleotides

| Strain/Plasmid | Genotype or Description | Source |
|---|---|---|
| Strains | | |
| *S. cerevisiae* WT | MATa/MATα; his3Δ1/his3Δ1; leu2Δ0/leu2Δ0; met15Δ0/MET15; LYS2/lys2Δ0; ura3Δ0/ura3Δ0 | Euroscarf #BY4743 |
| *S. cerevisiae* Δcyc1 | Mat a/α; his3Δ1/his3Δ1; leu2Δ0/leu2Δ0; lys2Δ0/LYS2; MET15/met15Δ0; ura3Δ0/ura3Δ0; YJR048w::kanMX4/YJR048w::kanMX4 | Euroscarf #Y36846 |
| *S. cerevisiae* Δcyc1-PpCyt c | *S. cerevisiae* Δcyc1 strain expressing *P. pastoris* cyt c (PpCyt c) | As provided herein |
| *S. cerevisiae* Δcyc1-ScCyt c | *S. cerevisiae* Δcyc1 strain expressing *S. cerevisiae* cyt c (ScCyt c) | As provided herein |
| *P. pastoris* (GS115) WT | his4 | Cregg et al., 1985, Mol. Cell Biol., 5:3376-3385 |
| *H. polymorpha* WT | prototroph | Dutch Centraal (CBS4732) Bureau Voor Schimmelcultures |
| Plasmids | | |
| pPS189 | multicopy expression vector with TEF2 promoter | Mumberg et al., 1995 (supra) |
| pPS-PpCyt c | pPS189 vector expressing PpCyt c | As provided herein |
| pPS-ScCyt c | pPS189 vector expressing ScCyt c | As provided herein |
| Oligonucleotides used for PCR amplification of PpCytc and ScCytc | | |
| PpCyt c-A | 5' GGATCCATGCCAGCTCCATACGAA 3' | As provided herein (SEQ ID NO: 13) |
| PpCyt c-B | 5' GAATTCCTATTTGGTGGCCTTGGCCAA 3' | As provided herein (SEQ ID NO: 14) |
| ScCyt c-A | 5' GGATCCATGACTGAATTCAAGGCC 3' | As provided herein (SEQ ID NO: 15) |
| ScCyt c-B | 5' CTCGAGTTACTCACAGGCTTTTTCAA 3' | As provided herein (SEQ ID NO: 16) |

As used herein, the abbreviations "PpCyt c" and "ScCyt c" denote *P. pastoris* cytochrome C and *S. cerevisiae* cytochrome C respectively. "*S. cerevisiae* cyc1ΔPpCyt c" and "*S. cerevisiae* cyc1Δ-ScCyt c", respectively denote *S. cerevisiae* cyc1Δ strain expressing PpCyt c and ScCyt c. That is, the host *S. cerevisiae* cell does not express its own endogenous cytochrome C (cyc1Δ), but has been transformed to express either the *P. pastoris* cytochrome C gene (PpCyt c) or a *S. cerevisiae* cytochrome C (ScCyt c). The abbreviation "Cyt c" as used herein is simply an abbreviation for cytochrome C.

Example 2

Construct Design

The recombinant plasmids expressing ScCyt c (pPS-ScCyt c) and PpCyt c (pPS-PpCyt c) were constructed as follows: RNA was isolated from *P. pastoris* GS115 and *S. cerevisiae* WT strains and used for obtaining cDNAs encoding *P. pastoris* cyt c (PpCyt c) and *S. cerevisiae* cyt c (ScCyt c) by RT-PCR respectively, using the primer pairs denoted below.

```
P. pastoris cytochrome C:
5' GGATCCATGCCAGCTCCATACGAA 3'     (SEQ ID NO: 13)
and

5' GAATTCCTATTTGGTGGCCTTGGCCAA 3'  (SEQ ID NO: 14)

S. cerevisiae cytochrome C.
5' GGATCCATGACTGAATTCAAGGCC 3'     (SEQ ID NO: 15)
and

5' CTCGAGTTACTCACAGGCTTTTTTCAA 3'  (SEQ ID NO: 16)
```

*P. pastoris* cytochrome C gene was isolated from *P. pastoris* genomic DNA by PCR using specific primers (SEQ ID NOS: 13 and 14), which were designed based on the *P. pastoris* genome sequence information available from Integrated Genomics genome database (ergo.integratedgenomics.com/ERGO/). *S. cerevisiae* cytochrome C gene was isolated from *S. cerevisiae* genomic DNA by PCR using specific primers (SEQ ID NOS: 15 and 16), which were designed based on the *S. cerevisiae* genome sequence information available from *Saccharomyces* genome database (yeastgenome.org).

Following restriction digestion of the PCR products, the cytochrome C cDNAs were cloned into pPS189 vector ((Mumberg, D. et al, *Gene,* 156:119-122, 1995), downstream of the constitutively active TEF2 promoter.

The recombinant plasmids expressing ScCyt c (pPS-ScCyt c) and PpCyt c (pPS-PpCyt c) were first propagated in *E. coli* (DH5α) and then transformed into *S. cerevisiae* cyc1Δ strain (*S. cerevisiae* strain. Y36846 (MATa/α;his3Δ1/his3Δ1; leu2Δ0/leu2Δ0; lys2Δ0/LYS2; MET15/met15Δ0;ura3Δ0/ura3Δ0;YJR048w::kanMX4/YJR048w::kanMX4) carrying null alleles in the CYC1 gene (Euroscarf, Germany) using lithium acetate.

Recombinant *S. cerevisiae* strains expressing PpCytc or ScCyt c (cyc1Δ-PpCyt c and cyc1Δ-ScCyt c) were selected for uracil auxotrophy and maintained on -RA YNBD agar plates.

Example 3

Assays

Expression of the recombinant gene encoding cytochrome C in the mitochondria of recombinant *S. cerevisiae* strains was confirmed by immunoflourescence using rabbit anti-cytochrome antibodies and FITC-conjugated anti-rabbit antibodies. Nuclei were visualized by staining with DAPI. Cytochrome C expression is detectable in the mitochondria of wild type (WT) and recombinant *S. cerevisiae* strains (cyc1Δ-PpCyt c and cyc1Δ-ScCyt c) but not in the *S. cerevisiae* strain lacking the endogenous cytochrome C gene (CYC1Δ).

Example 4

Figure 2A:
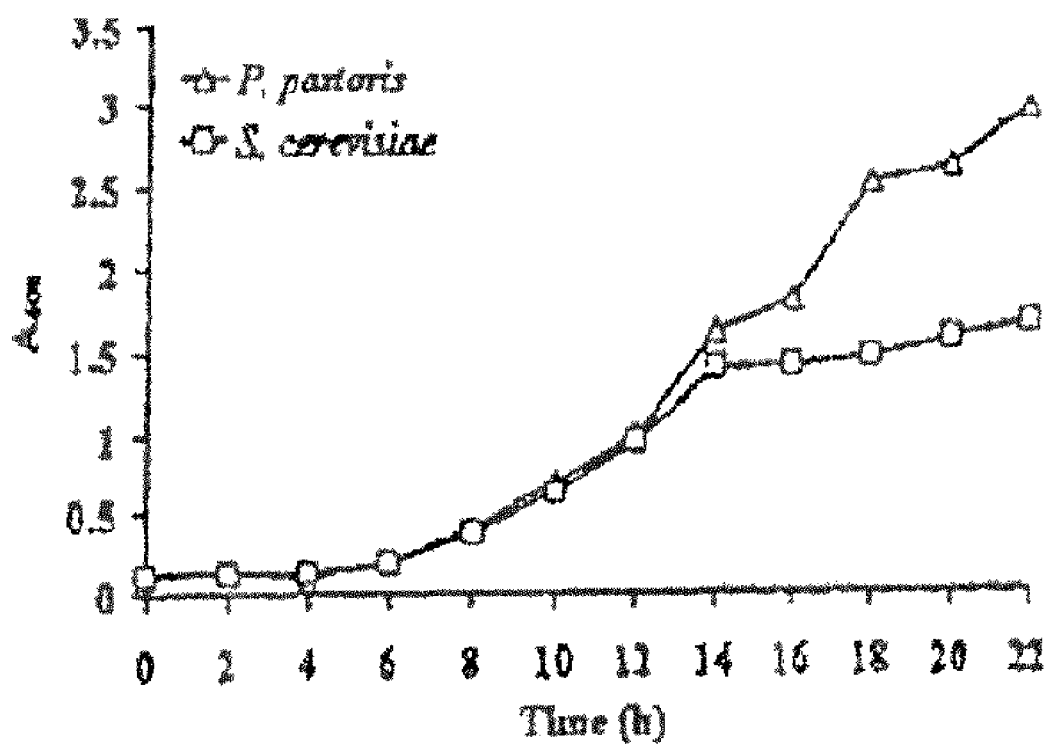
FIG. 2 is a series of growth curves for different yeast strains grown in YNBD medium containing glucose as the sole carbon source. (A) growth of wild-type *P. pastoris* and *S. cerevisiae* strains. (B) growth of *S. cerevisiae* cyc1Δ strain, *S. cerevisiae* cyc1Δ-PpCytc, and *S. cerevisiae* cyc1Δ-ScCytc in YNBD medium.
Figure 2B:
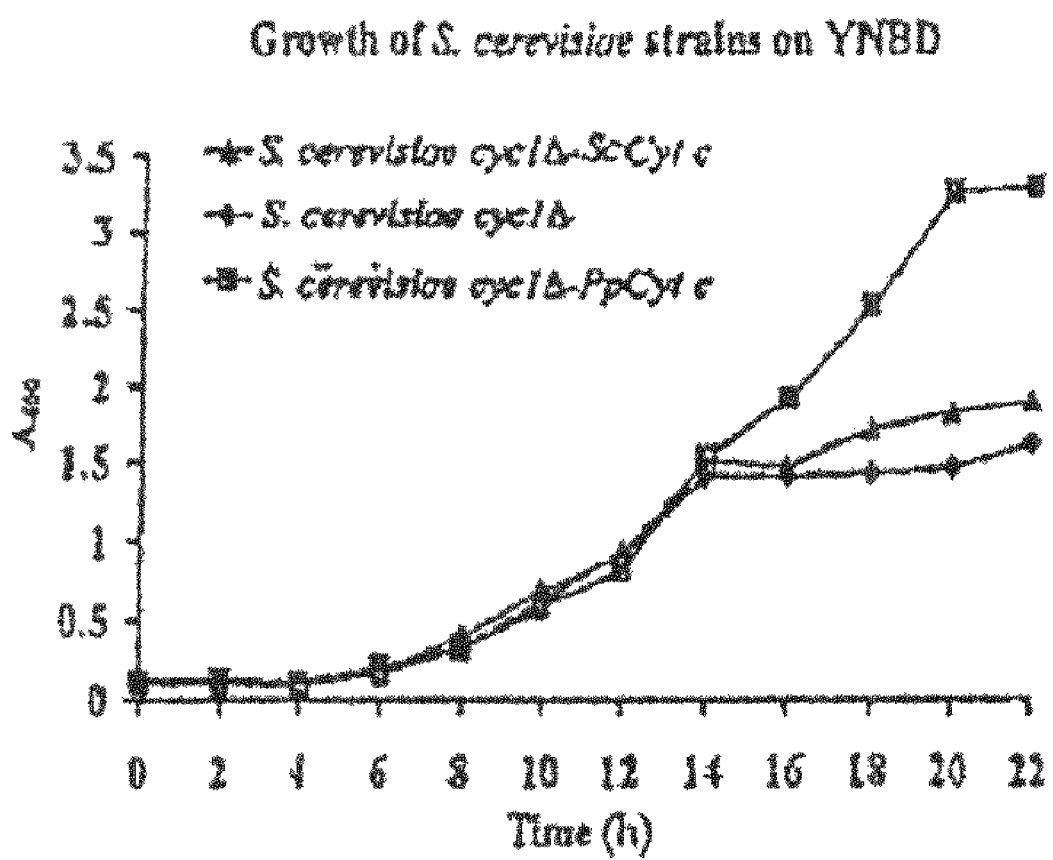

*P. pastoris* Cytochrome C Enhances the Growth of *S. Cerevisiae* Cells in Media Containing Oleic Acid or Glucose The growth of recombinant *S. cerevisiae* strains expressing PpCyt c or ScCyt c was compared with that of *S. cerevisiae* wild type (WT) and *P. pastoris* WT cells in YNBO or YNBD medium. The results indicate that *S. cerevisiae* cyc1Δ-PpCyt c cells grow more rapidly and attain higher cell densities than *S. cerevisiae* cyc1Δ-ScCyt c. Interestingly, the growth curve of *S. cerevisiae* cyc1Δ-PpCyt c was very similar to that of *P. pastoris* WT (see FIGS. 1 and 2).

Example 5

Figure 3A:
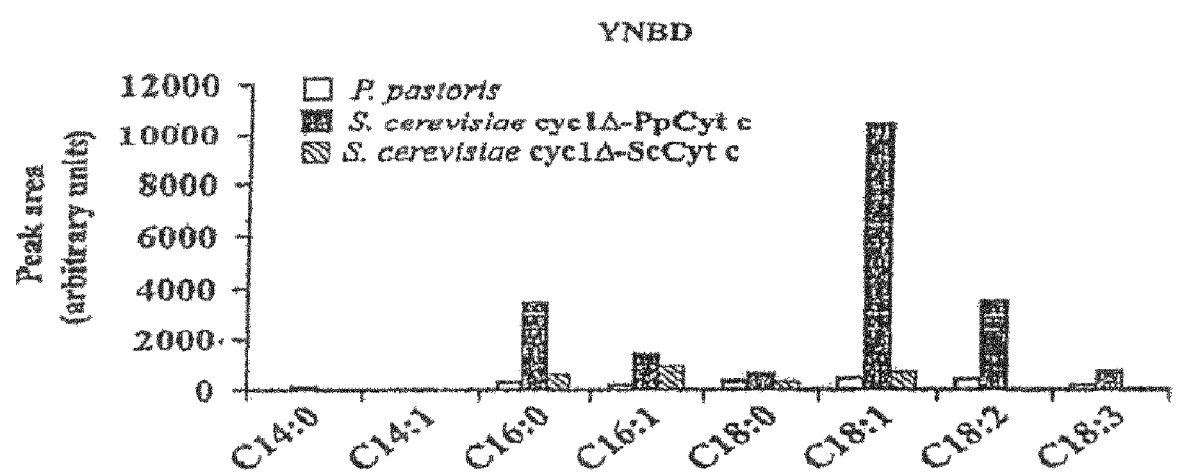
FIG. 3 shows the fatty acid composition of different yeast strains grown on YNBD (A) or YNBO (B) medium as determined by gas chromatography of fatty acid methyl esters. Lipids were extracted from 100 mg of yeast cells. Only major long chain fatty acids (C14-C18) are shown.
Figure 3B:
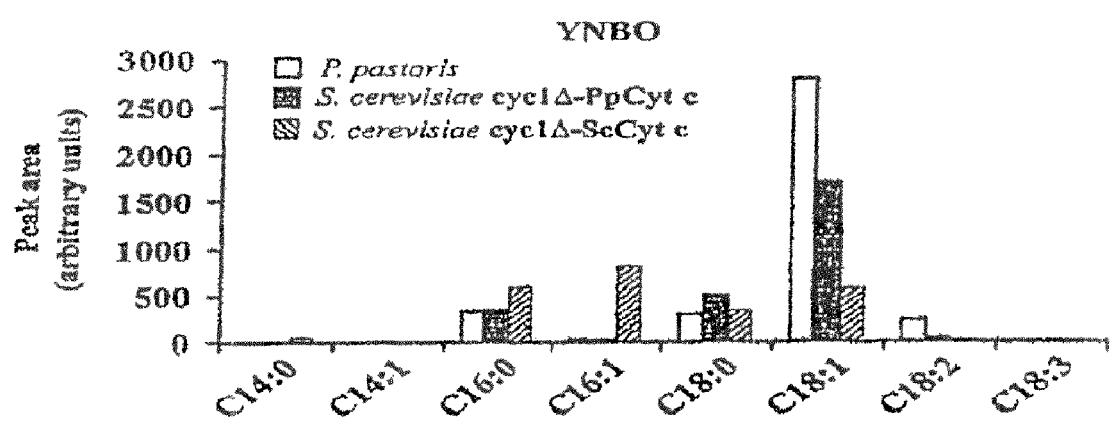

*P. pastoris* Cytochrome C Alters the Fatty Acid Composition of *S. cerevisiae* Cells To further understand the mechanism by which PpCyt c enhances the growth of *S. cerevisiae*, the fatty acid composition of recombinant *S. cerevisiae* strains were examined. When the recombinant yeast cells are grown on YNBD medium containing glucose as the sole carbon source, a dramatic increase (~20-fold) intracellular oleic acid (C18:1) level is observed in *S. cerevisiae* cyc1Δ-PpCyt c cells compared to that in *S. cerevisiae* cyc1Δ-ScCyt c cells as well as *P. pastoris* wild type strain (FIG. 3).

When yeast cells are grown on YNBO medium containing oleic acid as the sole carbon source, palmitoleic acid (C16:1) and oleic acid (C18:1) were found to be the most abundant monounsaturated fatty acids in *S. cerevisiae* cyc1Δ-ScCyt c cells as reported in the prior art (You et al., *Appl. Environ. Microbiol.,* 69:1499-1503, 2003). However, when PpCyt c is expressed in *S. cerevisiae* cells, palmitoleic acid levels are drastically reduced and oleic acid appears as the only major monounsaturated fatty acid in *S. cerevisiae* cyc1Δ-PpCyt c. Surprisingly, the monounsaturated fatty acid profile of *S. cerevisiae* cyc1Δ-PpCyt c strain is very similar to that of *P. pastoris* (FIG. 3). Thus, PpCyt c induces very significant changes in the fatty acid profile of *S. cerevisiae* cells.

Example 6

Figure 4:
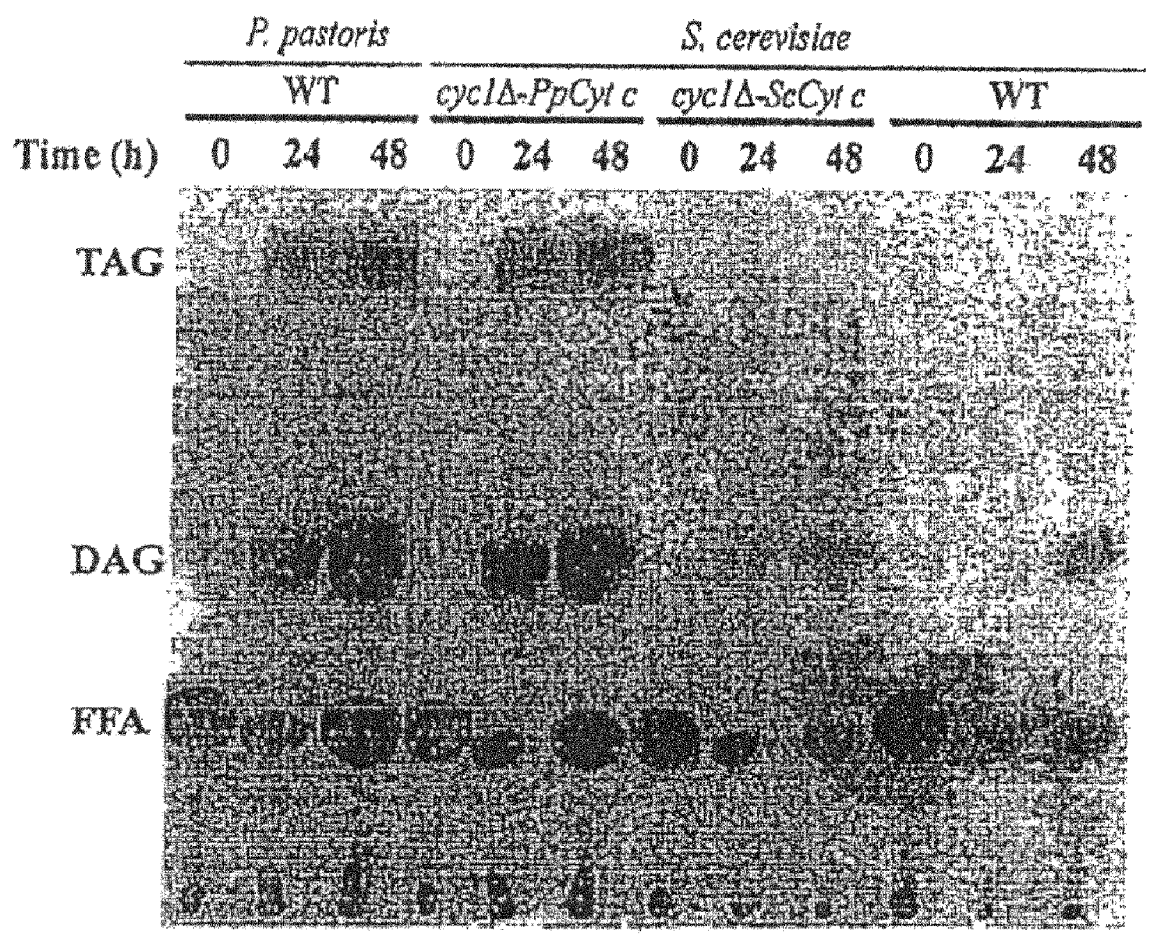
FIG. 4 shows analysis of neutral lipids of yeast cells grown on YNBO medium containing oleic acid as the sole carbon source using thin layer chromatography (TLC). Different yeast strains were grown on YNB+μCi/mL [1-$^{14}$C]oleic acid+ 0.05% unlabeled oleic acid emulsified with 0.005% Tween 40. Cells were withdrawn at different time points and $A_{600}$ was measured. Lipids were extracted from equal number of cells and analyzed by TLC using chloroform-methanol-acetic acid (98:2:0.5, v/v) as the solvent system. Lipids were identified by cochromatography with authentic standards. "FFA"=free fatty acids.

*S. cerevisiae* Cells Expressing *P. pastoris* Cytochrome C Accumulate Higher Itracellular Levels of Diacylglycerol and Triacylglycerol than those Expressing Endogenous *S. cerevisiae* Cytochrome C alone When yeast cells are cultured in YNBO medium in the presence of [$^{14}$C]-oleic acid, *S. cerevisiae* cyc1ΔPpCyt c and *P. pastoris* WT strains were found to accumulate more oleic acid, DAG and TAG than *S. cerevisiae* cyc1Δ-ScCyt c or *S. cerevisiae* WT cells (FIG. 4).

Figure 5:
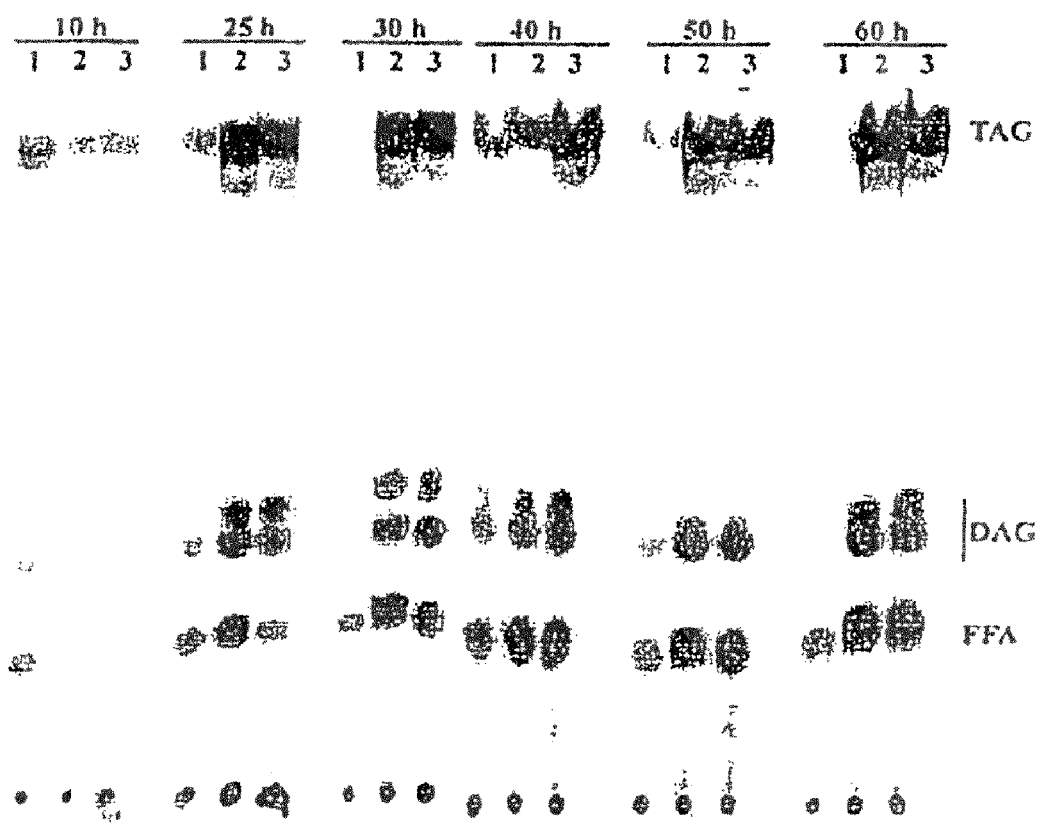
FIG. 5 shows analysis of neutral lipids of yeast cells grown on YNBD medium containing glucose as the sole carbon source by TLC. Different yeast strains were grown on YNB+ $^{14}$C-glucose, cells were withdrawn at different time points and $A_{600}$ was measured. Lipids were extracted from equal number of cells and analyzed by TLC using chloroform-methanol-acetic acid (98:2-0.5, v/v) as the solvent system. Lipids were identified by cochromatography with authentic standards. Lane 1, *S. cerevisiae* cyc1Δ-ScCyt C cells; Lane 2, *S. cerevisiae* cyc1Δ-PpCyt C cells; Lane 3, *P. pastoris* cells. "FFA"=free fatty acids.

When yeast cells are cultured in YNBD medium in presence of 14C-glucose, *S. cerevisiae* cyc1☐-PpCyt c cells were found to incorporate $^{14}$C-glucose into diacylglycerol and triacylglycerol more rapidly than *S. cerevisiae* cyc1Δ-ScCyt c cells (FIG. 5). Surprisingly, a similar pattern was observed in *P. pastoris* cells as well indicating that PpCyt c induces as *P. pastoris*-like phenotype to *S. cerevisiae* cells. To the contrary, incorporation of $^{14}$C-glucose into diacylglycerol and triacylglycerol was very low in *S. cerevisiae* cyc1Δ-ScCyt c cells and is barely detectable in the autoradiogram (FIG. 5).

Example 7

*P. pastoris* Cytochrome C Enhances the Biomass of *S. cerevisiae* Cells

Figure 6:
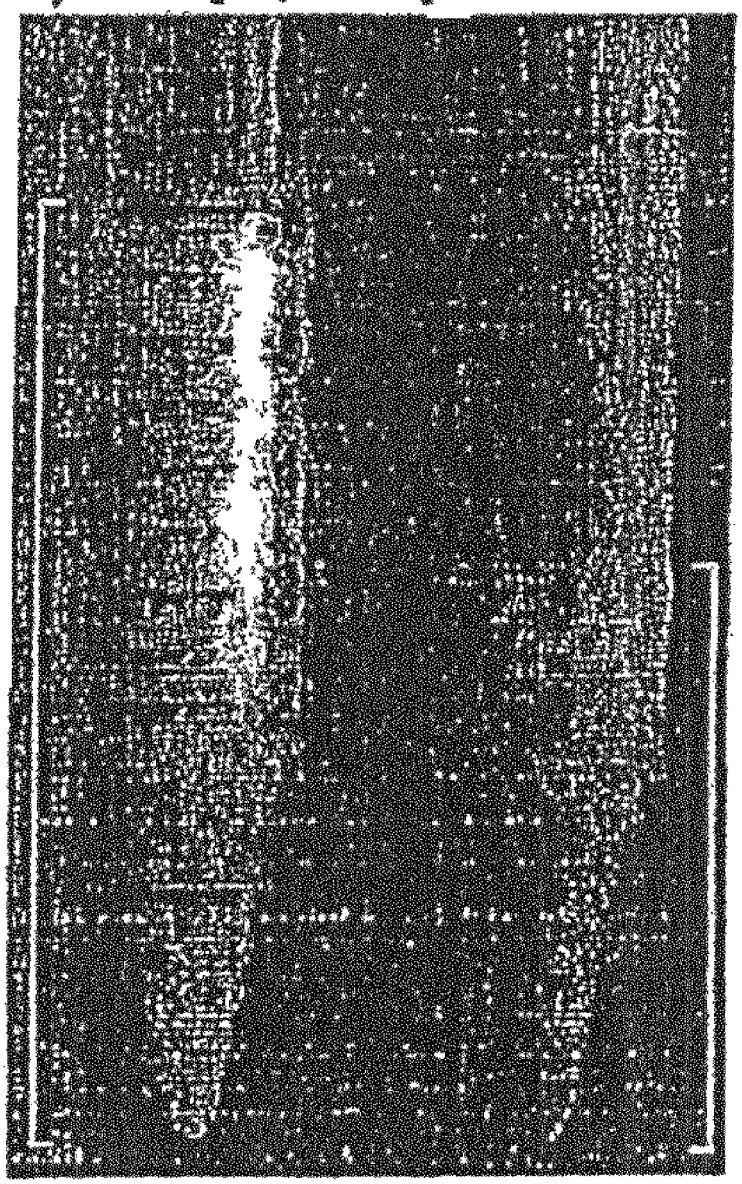
FIG. 6 is a photograph of *S. cerevisiae* strains grown on YNBD medium for 36 hours in shaker flasks with vigorous shaking. Cells were centrifuged and the packed cell volume measured in graduated tubes as shown.
Figure 9:
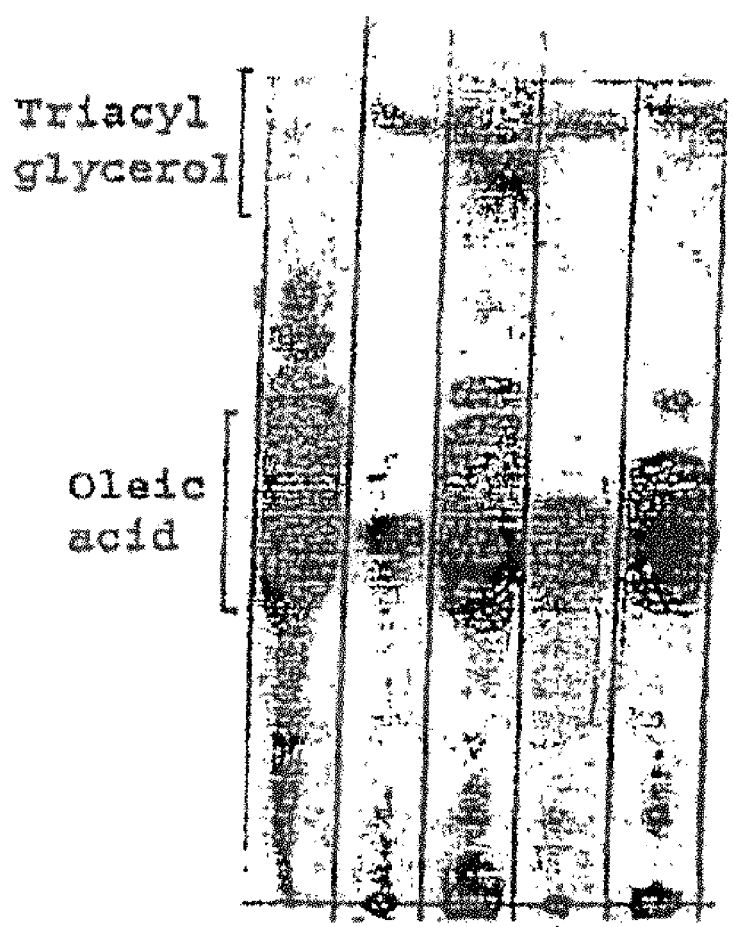
FIG. 9 shows, using TLC, oleic acid accumulation induced by the expression of *P. pastoris* cytochrome C in *S. cerevisiae* cells expressing endogenous cytochrome C (WT) as well as cells that do not express endogenous cytochrome C (cyc1 Δ). Different yeast strains were frown on YNBD for 48 hours and $A_{600}$ was measured. Lipids were extracted from equal number of cells and analyzed by TLC using chloroform-methanol-acetic acid (98:2:0.5, v/v) as the solvent system. Lipids were visualized by exposing the TLC plate briefly to iodine vapors. Oleic acid and triacylglycerol were identified by cochromatography with authentic standards. Lane 1, oleic acid standard; Lane 2, *S. cerevisiae* cyc1 Δ cells; Lane 3, *S. cerevisiae* cyc1Δ-PpCyt C cells; Lane 4, *S. cerevisiae* WT cells; Lane 5, *S. cerevisiae* WT-PpCyt C cells.

The packed cell volume (PCV) of *S. cerevisiae* cyc1Δ-PpCyt c strain grown in shaker flasks in YNBD medium containing glucose as the sole carbon source is at least two fold higher than that of *S. cerevisiae* cyc1Δ-ScCyt c strain (FIG. 6).

Example 8

*P. pastoris* Cytochrome C Localizes to Peroxisomes of *P. pastoris* Cells Cultured in a Medium Containing Methanol as the Sole Carbon Source The extramitochondrial localization of PpCyt c in *P. pastoris* cells grown in YNBM medium containing methanol as the sole carbon source, prompted an examination of its exact intracellular localization. Immunoflourescence studies were carried out with anti-cyt c antibodies in presence of organelle-specific markers. It was expected that PpCyt c may localize to the nucleus of *P. pastoris* cells grown in YNBM medium. The results indicated that PpCyt c was present in the mitochondria of *P. pastoris* cells grown on dextrose (YNBD) as expected. However, contrary to expectations, PpCyt c did not colocalize with DAPI, a nuclear marker. Surprisingly, its distribution in cells grown on YNBM resembled that of alcohol oxidase (AOX), a well known peroxisomal protein whose expression is induced by methanol. This was confirmed by colocalization studies using anti-cyt c and anti-AOX antibodies. Both cyt c and AOX were found to localize to the peroxisomes of *P. pastoris* cells grown on YNBM.

Peroxisomal localization of PpCyt c was further confirmed by biochemical studies in which peroxisomes were purified from *P. pastoris* cells grown on YNBM, peroxisomal proteins were resolved on a 2-dimensional polyacrylamide gel and subjected to Western blot analysis using anti-cyt c antibodies. A protein immunoreactive to anti-cyt c antibodies having molecular weight and pI similar to that of cyt c purified from *S. cerevisiae* was present in *P. pastoris* peroxisomes, Example 9

*P. pastoris* Cytochrome C Localizes to Peroxisomes of *P. pastoris* Cells Cultured in a Medium Containing Long Chain Fatty Acids as the Sole Carbon Source AOX expression and peroxisome proliferation are induced not only by methanol but also by long chain fatty acids in *P. pastoris* (Kobayashi et al., *J. Biosci. Bioeng.,* 89:479-84, 2000). Therefore PpCyt c localization studies were carried out in *P. pastoris* cells grown on stearic acid (YNBS) or oleic acid (YNBO) as the sole carbon source. The results indicate that Ppcyt c and AOX colocalize to fatty acid-induced peroxisomes as well.

Example 10

Peroxisomal Localization of Cytochrome C is not Observed in *cerevisiae* or Polymorpha To examine whether peroxisomal localization of cyt c is a general property of all the yeast species, immunoflourescence studies were carried out in other yeast species. Cyt c was localized in the mitochondria and not peroxisomes of oleic acid-grown *S. cerevisiae* or methanol-grown *Hansenula polymorpha*, another methylotrophic yeast, indicating that peroxisomal localization of cyt c is a unique feature of *P. pastoris*.

The results obtained from immunoflourescence studies was further confirmed by immunoelectron microscopy. Both PpCyt c and AOX were found to colocalize to peroxisomes of *P. pastoris* cells grown on methanol.

Example 11

*P. pastoris* Cytochrome C can be Targeted to the Peroxisomes of *S. cerevisiae*

The nucleotide sequence of gene encoding PpCyt c (RPPA05914, Contig1492_101916_101581) was obtained from Integrated genomics *P. pastoris* genome database (ergo.integratedgenomics.com/ERGO/; see SEQ ID NO:1 (Genbank Accession No. EU735068)). This nucleotide sequence was further confirmed by sequencing the PpCyt c EDNA obtained by PCR product. The PpCyt c amino acid sequence is depicted in SEQ ID NO:2 (Genbank Accession No. ACE75949).

The amino acid sequence of *S. cerevisiae* cyt c is available as accession #CAA89576 and is depicted in SEQ ID NO:3.

Comparison of SEQ ID NOS: 2 and 3 indicated 77% identity between the *P. pastoris* and *S. cerevisiae* cytochrome C sequences (FIG. 7).

Despite the high degree of identity between PpCyt c and *S. cerevisiae* cyt c (ScCyt c) amino acid sequences it was surprising that peroxisomal targeting of cyt c was observed only in *P. pastoris* but not *S. cerevisiae*. *S. cerevisiae* cyc1Δ strain, which does not express ScCyt c encoded by cyc1 gene, was therefore used as a surrogate model to understand the biochemical properties of PpCyt c.

The cDNAs encoding PpCyt c and ScCyt c were cloned into pPS189 vector under the control of constitutively active TEF2 promoter (Mumberg et al., *Gene,* 156.119-122, 1995), using standard cloning protocols, The recombinant plasmids were transformed into *S. cerevisiae* cyc1Δ strain and when the recombinant *S. cerevisiae* strains expressing PpCyt c and ScCyt c (designated herein as *S. cerevisiae* cyc1ΔPpCyt c and *S. cerevisiae* cyc1Δ-ScCyt c respectively) were grown on YNBD medium containing glucose as the sole carbon source, cyt c was localized in the mitochondria as expected, When *S cerevisiae* cyc1Δ-PpCyt c and *S. cerevisiae* cyc1Δ-ScCyt c strains were grown on YNBO medium containing oleic acid as the sole carbon source, however, only PpCyt c (expressed in *S. cerevisiae* cyc1Δ-PpCyt c strain) but not ScCyt c (expressed in *S. cerevisiae* cyc1Δ-ScCyt c strain) was localized in the peroxisomes.

The peroxisomal localization of PpCyt c was confirmed by the fact that its immunolocalization pattern was similar to that of thiolase, a well characterized peroxisomal enzyme (Erdmann, R. and Kunau, W., *Yeast,* 10:1173-1182, 1994). Peroxisomal localization was unique to PpCyt c, since other mitochondrial proteins such as porin and HSP70 were present in mitochondria under similar conditions, The results obtained from immunoflourescence studies were further confirmed by biochemical fractionation studies. Peroxisomes and mitochondria were purified from *S. cerevisiae* cyc1Δ-PpCyt c and *S. cerevisiae* cyc1Δ-ScCyt c cells on nycodenz gradients and their identity was confirmed by western blot analysis using organelle-specific marker antibodies.

Since c-type cytochromes retain their heme groups due to covalent linkages even under denaturating conditions, the peroxisomal proteins were resolved on a SDS polyacrylamide gel and stained with tetramethylbenzidine to detect holocyt c. A band co-migrating with cyt c purified from S. cerevisiae cells was observed in the peroxisomes of S. cerevisiae cyc1Δ-PpCyt c but not S. cerevisiae cyc1Δ-ScCyt c indicating that PpCyt c is present in the peroxisomes of S. cerevisiae cyc1-PpCyt c as holocyt c with covalently attached heme.

What is claimed is:

1. A recombinant yeast cell comprising a recombinant expression cassette that expresses a gene encoding a cytochrome C polypeptide, wherein the cytochrome C polypeptide has at least 95% identity to SEQ ID NO. 2.

2. The recombinant yeast cell of claim 1, wherein the gene encoding the cytochrome C polypeptide is a *Pichia pastoris* cytochrome C gene.

3. The recombinant yeast cell of claim 1, wherein the gene encoding the cytochrome C polypeptide is operably linked to at least one gene regulatory element in the gene expression cassette.

4. The recombinant yeast cell of claim 1, wherein the expression cassette that expresses the gene encoding the cytochrome C polypeptide is an extrachromosomal self-replicating vector.

5. The recombinant yeast cell of claim 1, wherein the yeast cell is *Saccharomyces cerevisiae*.

6. The recombinant yeast cell of claim 1, wherein the gene encoding the cytochrome C polypeptide is encoded by SEQ ID NO: 1.

7. The recombinant yeast cell of claim 1, wherein the cytochrome C polypeptide is SEQ ID NO: 2.

8. The recombinant yeast cell of claim 1, wherein the recombinant cell further comprises a second recombinant gene cassette that expresses a target gene.

9. The recombinant yeast cell of claim 8, wherein the target gene is integrated into the cell genome or expressed extrachromosomally in a self-replicating plasmid.

10. The recombinant yeast cell of claim 8, wherein the target gene is a hepatitis B surface antigen gene, an insulin gene or an erythropoietin gene.

11. A method for producing a polyunsaturated fatty acid molecule in a recombinant yeast cell, comprising growing a recombinant yeast cell comprising a recombinant expression cassette that expresses a gene encoding a cytochrome C polypeptide, wherein the cytochrome C polypeptide has at least 95% identity to SEQ ID NO. 2, under conditions wherein a polyunsaturated fatty acid is produced.

12. The method of claim 11, wherein the polyunsaturated fatty acid is selected from the group consisting of: a linoleic acid, a linolenic acid, an omega-3 fatty acid and an omega-6 fatty acid.

13. The method of claim 11, wherein the recombinant yeast cell does not express an endogenous gene encoding a biologically active cytochrome C polypeptide.

14. The method of claim 11, further comprising:
extracting the polyunsaturated fatty acid from the recombinant yeast cell, wherein the recombinant yeast cell is either grown on an oleic acid substrate or grown on a glucose substrate for at least about 12 hours before being grown on an oleic acid substrate.

15. A method of producing an isolated cytochrome C polypeptide comprising:
   a) culturing a recombinant yeast cell comprising a recombinant expression cassette that expresses a gene encoding a cytochrome C polypeptide, wherein the cytochrome C polypeptide has at least 95% identity to SEQ ID NO. 2, under conditions wherein the yeast cell expresses the cytochrome C polypeptide, and
   b) isolating the cytochrome C polypeptide, thereby producing an isolated cytochrome C polypeptide.

16. The method of claim 15, wherein the recombinant yeast cell is cultured on a glucose-containing substrate for more than about 12 hours.

17. The method of claim 15, wherein the recombinant expression cassette has a polynucleotide sequence that encodes a signal or secretion peptide, wherein the expressed cytochrome C polypeptide is transported out of or secreted from the recombinant yeast cell.

18. The method of claim 15, wherein step b) comprises centrifuging an aliquot of the yeast cell culture and then purifying the cytochrome C polypeptide from the culture supernatant.

* * * * *

UNITED STATES PATENT AND TRADEMARK OFFICE
CERTIFICATE OF CORRECTION

PATENT NO. : 7,892,792 B2  
APPLICATION NO. : 12/491909  
DATED : February 22, 2011  
INVENTOR(S) : Rangarajan et al.

It is certified that error appears in the above-identified patent and that said Letters Patent is hereby corrected as shown below:

On the Title Page, item (75), under "Inventors", in Column 1, Line 1, delete "Bangladore" and insert -- Bangalore --, therefor.

On the Title Page, item (75), under "Inventors", in Column 1, Line 2, delete "Bangladore" and insert -- Bangalore -- therefor.

On the Title Page, item (56), under "OTHER PUBLICATIONS", in Column 2, Line 2, delete "cytochrom" and insert -- cytochrome --, therefor.

In Column 1, Line 24, delete "although" and insert -- although, --, therefor.

In Column 1, Line 53, delete "extracbromosomally" and insert -- extrachromosomally --, therefor.

In Column 1, Line 61, delete "farther" and insert -- further --, therefor.

In Column 1, Line 64, delete "cytochlome" and insert -- cytochrome --, therefor.

In Column 4, Line 23, delete "(98:2-0.5," and insert -- (98:2:0.5, --, therefor.

In Column 4, Line 38, delete "order)," and insert -- order). --, therefor.

In Column 5, Line 5, delete "glucose," and insert -- glucose; --, therefor.

In Column 5, Line 26, delete "e,g.," and insert -- e.g., --, therefor.

In Column 6, Line 28, delete "e.g." and insert -- e.g., --, therefor.

In Column 6, Line 30, delete "e.g," and insert -- e.g., --, therefor.

Signed and Sealed this  
Eighth Day of May, 2012

David J. Kappos  
*Director of the United States Patent and Trademark Office*

Page 1 of 3

CERTIFICATE OF CORRECTION (continued)
U.S. Pat. No. 7,892,792 B2

In Column 8, Line 7, delete "(GCC)," and insert -- (GCG), --, therefor.

In Column 8, Line 24, delete "Mol" and insert -- Mol. --, therefor.

In Column 8, Line 27, delete "e.g," and insert -- e.g., --, therefor.

In Column 9, Line 26, delete "system" and insert -- system. --, therefor.

In Column 9, Line 43, delete "art" and insert -- art. --, therefor.

In Column 10, Line 2, delete "construct" and insert -- construct. --, therefor.

In Column 10, Line 20, delete "cells" and insert -- cells. --, therefor.

In Column 10, Line 24, delete "expressed" and insert -- expressed. --, therefor.

In Column 10, Line 38, delete "guiliermondii," and insert -- guilliermondii --, therefor.

In Column 10, Line 39, delete "lactic," and insert -- lactis, --, therefor.

In Column 10, Line 47, delete "cytochirome" and insert -- cytochrome --, therefor.

In Column 11, Line 52, delete "Proc," and insert -- Proc. --, therefor.

In Column 11, Line 64, delete "5-40" and insert -- 15-40 --, therefor.

In Column 12, Line 31, delete "A600" and insert -- $A_{600}$ --, therefor.

In Column 14, Line 11, delete "1 0-fold," and insert -- 10-fold, --, therefor.

In Column 14, Line 30, delete "novo" and insert -- novo. --, therefor.

In Column 14, Line 49, delete "eicosatetracnoic" and insert -- eicosatetraenoic --, therefor.

In Column 16, Line 3, delete "acid," and insert -- acid. --, therefor.

In Column 17, Line 39, delete "al," and insert -- al., --, therefor.

In Column 17, Line 52, delete "-RA YNBD" and insert -- URA-YNBD --, therefor.

In Column 19, Line 16, delete "P" and insert -- P. --, therefor.

In Column 19, Line 44, delete "peroxisomes," and insert -- peroxisomes. --, therefor.

CERTIFICATE OF CORRECTION (continued)
U.S. Pat. No. 7,892,792 B2

In Column 20, Line 23, delete "EDNA" and insert -- cDNA --, therefor.

In Column 20, Line 32, delete "sequences" and insert -- sequences, --, therefor.

In Column 20, Line 40, delete "156.119-112," and insert -- 156:119-112, --, therefor.

In Column 20, Line 41, delete "protocols," and insert -- protocols. --, therefor.

In Column 20, Line 48, delete "expected," and insert -- expected. --, therefor.

In Column 20, Line 49, delete "S" and insert -- S. --, therefor.

In Column 20, Line 61, delete "conditions," and insert -- conditions. --, therefor.

SEQUENCE LISTING

<160> NUMBER OF SEQ ID NOS: 20

<210> SEQ ID NO 1
<211> LENGTH: 333
<212> TYPE: DNA
<213> ORGANISM: Pichia pastoris

<400> SEQUENCE: 1

```
atgccagctc catacgaaaa aggttcagag aagaaaggtg ctactttgtt caagaccaga      60
tgtctgcaat gtcacactgt cgaggctggt ggaccacaca aagttggtcc taacttgcat     120
ggtgtcttcg gaagaaagtc tggtttggct gagggatact cttacaccga tgccaacaag     180
agaaagggag ttgaatggtc cgagcaaacc atgtccgact acttggagaa cccaaagaag     240
tacattccag gaaccaagat ggctttcggt ggtctaaaga aggccaagga cagaaacgac     300
ttgattacct acttggccaa ggccaccaaa tag                                   333
```

<210> SEQ ID NO 2
<211> LENGTH: 110
<212> TYPE: PRT
<213> ORGANISM: Pichia pastoris

<400> SEQUENCE: 2

```
Met Pro Ala Pro Tyr Glu Lys Gly Ser Glu Lys Lys Gly Ala Thr Leu
1               5                   10                  15

Phe Lys Thr Arg Cys Leu Gln Cys His Thr Val Glu Ala Gly Gly Pro
                20                  25                  30

His Lys Val Gly Pro Asn Leu His Gly Val Phe Gly Arg Lys Ser Gly
            35                  40                  45

Leu Ala Glu Gly Tyr Ser Tyr Thr Asp Ala Asn Lys Arg Lys Gly Val
        50                  55                  60

Glu Trp Ser Glu Gln Thr Met Ser Asp Tyr Leu Glu Asn Pro Lys Lys
65                  70                  75                  80

Tyr Ile Pro Gly Thr Lys Met Ala Phe Gly Gly Leu Lys Lys Ala Lys
                85                  90                  95

Asp Arg Asn Asp Leu Ile Thr Tyr Leu Ala Lys Ala Thr Lys
            100                 105                 110
```

<210> SEQ ID NO 3
<211> LENGTH: 109
<212> TYPE: PRT
<213> ORGANISM: Saccharomyces cerevisiae

<400> SEQUENCE: 3

```
Met Thr Glu Phe Lys Ala Gly Ser Ala Lys Lys Gly Ala Thr Leu Phe
1               5                   10                  15

Lys Thr Arg Cys Leu Gln Cys His Thr Val Glu Lys Gly Gly Pro His
                20                  25                  30

Lys Val Gly Pro Asn Leu His Gly Ile Phe Gly Arg His Ser Gly Gln
            35                  40                  45

Ala Glu Gly Tyr Ser Tyr Thr Asp Ala Asn Ile Lys Lys Asn Val Leu
        50                  55                  60
```

```
Trp Asp Glu Asn Asn Met Ser Glu Tyr Leu Thr Asn Pro Lys Lys Tyr
 65                  70                  75                  80

Ile Pro Gly Thr Lys Met Ala Arg Gly Gly Leu Lys Lys Glu Lys Asp
                 85                  90                  95

Arg Asn Asp Leu Ile Thr Tyr Leu Lys Lys Ala Cys Glu
            100                 105

<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (29)..(29)
<223> OTHER INFORMATION: Ala, Glu or Lys
<220> FEATURE:
<221> NAME/KEY: MOD_RES
<222> LOCATION: (67)..(67)
<223> OTHER INFORMATION: Ser or Thr

<400> SEQUENCE: 4

Met Pro Ala Pro Tyr Glu Lys Gly Ser Glu Lys Lys Gly Ala Thr Leu
  1               5                  10                  15

Phe Lys Thr Arg Cys Leu Gln Cys His Thr Val Glu Xaa Gly Gly Pro
             20                  25                  30

His Lys Val Gly Pro Asn Leu His Gly Val Phe Gly Arg Lys Ser Gly
             35                  40                  45

Gln Ala Glu Gly Tyr Ser Tyr Thr Asp Ala Asn Lys Lys Lys Gly Val
         50                  55                  60

Glu Trp Xaa Glu Gln Thr Met Ser Asp Tyr Leu Glu Asn Pro Lys Lys
 65                  70                  75                  80

Tyr Ile Pro Gly Thr Lys Met Ala Phe Gly Gly Leu Lys Lys Ala Lys
                 85                  90                  95

Asp Arg Asn Asp Leu Val Thr Tyr Leu Ala Lys Ala Thr Lys
            100                 105                 110

<210> SEQ ID NO 5
<211> LENGTH: 110
<212> TYPE: PRT
<213> ORGANISM: Debaryomyces hansenii

<400> SEQUENCE: 5

Met Pro Ala Pro Tyr Glu Lys Gly Ser Glu Lys Lys Gly Ala Asn Leu
  1               5                  10                  15

Phe Lys Thr Arg Cys Leu Gln Cys His Thr Val Glu Glu Gly Gly Pro
             20                  25                  30

His Lys Val Gly Pro Asn Leu His Gly Val Val Gly Arg Thr Ser Gly
             35                  40                  45

Gln Ala Gln Gly Phe Ser Tyr Thr Asp Ala Asn Lys Lys Lys Gly Val
         50                  55                  60

Glu Trp Ser Glu Gln Asn Leu Ser Asp Tyr Leu Glu Asn Pro Lys Lys
 65                  70                  75                  80

Tyr Ile Pro Gly Thr Lys Met Ala Phe Gly Gly Leu Lys Lys Ala Lys
                 85                  90                  95

Asp Arg Asn Asp Leu Ile Ser Tyr Leu Val Lys Ala Thr Lys
            100                 105                 110
```

<210> SEQ ID NO 6
<211> LENGTH: 110
<212> TYPE: PRT
<213> ORGANISM: Debaryomyces occidentalis

<400> SEQUENCE: 6

Met Pro Ala Pro Tyr Glu Lys Gly Ser Glu Lys Lys Asp Ala Asn Leu
1               5                   10                  15

Phe Lys Thr Arg Cys Leu Gln Cys His Thr Val Glu Lys Gly Gly Pro
            20                  25                  30

His Lys Val Gly Pro Asn Leu His Gly Ile Phe Gly Arg Lys Ser Gly
        35                  40                  45

Gln Ala Ala Gly Tyr Ser Tyr Thr Asp Ala Asn Lys Lys Lys Gly Val
    50                  55                  60

Glu Trp Thr Glu Gln Thr Met Ser Asp Tyr Leu Glu Asn Pro Lys Lys
65                  70                  75                  80

Tyr Ile Pro Gly Thr Lys Met Ala Phe Gly Leu Lys Lys Pro Lys Lys
                85                  90                  95

Asp Arg Asn Asp Leu Ile Thr Tyr Leu Ala Asn Ala Thr Lys
            100                 105                 110

<210> SEQ ID NO 7
<211> LENGTH: 110
<212> TYPE: PRT
<213> ORGANISM: Pichia guilliermondii

<400> SEQUENCE: 7

Met Pro Ala Pro Tyr Glu Lys Gly Ser Glu Lys Lys Gly Ala Thr Leu
1               5                   10                  15

Phe Lys Thr Arg Cys Leu Gln Cys His Thr Val Glu Glu Gly Ala Pro
            20                  25                  30

Asn Lys Val Gly Pro Asn Leu His Gly Leu Ile Gly Arg Lys Ser Gly
        35                  40                  45

Gln Val Glu Gly Tyr Ser Tyr Thr Asp Ala Asn Lys Lys Lys Gly Val
    50                  55                  60

Glu Trp Thr Glu Gln Asn Leu Ser Asp Tyr Leu Glu Asn Pro Lys Lys
65                  70                  75                  80

Tyr Ile Pro Gly Thr Lys Met Ala Phe Gly Leu Lys Lys Ala Lys
                85                  90                  95

Asp Arg Asn Asp Leu Ile Thr Tyr Leu Val Ser Ala Thr Lys
            100                 105                 110

<210> SEQ ID NO 8
<211> LENGTH: 110
<212> TYPE: PRT
<213> ORGANISM: Pichia stipitis

<400> SEQUENCE: 8

Met Pro Ala Pro Phe Glu Lys Gly Ser Glu Lys Lys Gly Ala Thr Leu
1               5                   10                  15

Phe Lys Thr Arg Cys Leu Gln Cys His Thr Val Glu Glu Gly Gly Pro
            20                  25                  30

His Lys Val Gly Pro Asn Leu His Gly Ile Met Gly Arg Lys Ser Gly
        35                  40                  45

Gln Ala Val Gly Tyr Ser Tyr Thr Asp Ala Asn Lys Lys Lys Gly Val
    50                  55                  60

Glu Trp Ser Glu Gln Thr Met Ser Asp Tyr Leu Glu Asn Pro Lys Lys

```
                65                  70                  75                  80
Tyr Ile Pro Gly Thr Lys Met Ala Phe Gly Gly Leu Lys Lys Pro Lys
                    85                  90                  95
Asp Arg Asn Asp Leu Val Thr Tyr Leu Ala Ser Ala Thr Lys
            100                 105                 110

<210> SEQ ID NO 9
<211> LENGTH: 110
<212> TYPE: PRT
<213> ORGANISM: Candida albicans

<400> SEQUENCE: 9

Met Pro Ala Pro Phe Glu Lys Gly Ser Glu Lys Lys Gly Ala Thr Leu
1               5                   10                  15
Phe Lys Thr Arg Cys Leu Gln Cys His Thr Val Glu Lys Gly Gly Pro
                20                  25                  30
His Lys Val Gly Pro Asn Leu His Gly Val Phe Gly Arg Lys Ser Gly
            35                  40                  45
Leu Ala Glu Gly Tyr Ser Tyr Thr Asp Ala Asn Lys Lys Gly Val
        50                  55                  60
Glu Trp Thr Glu Gln Thr Met Ser Asp Tyr Leu Glu Asn Pro Lys Lys
65                  70                  75                  80
Tyr Ile Pro Gly Thr Lys Met Ala Phe Gly Gly Leu Lys Lys Pro Lys
                    85                  90                  95
Asp Arg Asn Asp Leu Val Thr Tyr Leu Lys Lys Ala Thr Ser
            100                 105                 110

<210> SEQ ID NO 10
<211> LENGTH: 110
<212> TYPE: PRT
<213> ORGANISM: Kluyveromyces lactis

<400> SEQUENCE: 10

Met Pro Ala Pro Tyr Lys Lys Gly Ser Glu Lys Lys Gly Ala Thr Leu
1               5                   10                  15
Phe Lys Thr Arg Cys Leu Gln Cys His Thr Val Glu Ala Gly Gly Pro
                20                  25                  30
His Lys Val Gly Pro Asn Leu His Gly Val Phe Gly Arg His Ser Gly
            35                  40                  45
Lys Ala Ser Gly Tyr Ser Tyr Thr Asp Ala Asn Ile Lys Lys Asn Val
        50                  55                  60
Leu Trp Asp Glu Gln Thr Met Ser Asp Tyr Leu Glu Asn Pro Lys Lys
65                  70                  75                  80
Tyr Ile Pro Gly Thr Lys Met Ala Phe Gly Gly Leu Lys Lys Glu Lys
                    85                  90                  95
Asp Arg Asn Asp Ile Val Thr Tyr Met Leu Lys Ala Cys Lys
            100                 105                 110

<210> SEQ ID NO 11
<211> LENGTH: 110
<212> TYPE: PRT
<213> ORGANISM: Pachysolen tannophilus

<400> SEQUENCE: 11

Met Pro Ala Pro Tyr Glu Lys Gly Ser Ala Lys Lys Gly Ala Thr Leu
1               5                   10                  15
Phe Lys Thr Arg Cys Leu Gln Cys His Thr Thr Glu Ala Gly Gly Ala
                20                  25                  30
```

His Lys Val Gly Pro Asn Leu Asn Gly Val Phe Gly Arg His Ser Gly
            35                  40                  45

Gln Ala Glu Gly Tyr Ser Tyr Thr Asp Ala Asn Lys Gln Lys Gly Ala
        50                  55                  60

Leu Trp Glu Ala Gln Thr Met Ser Asp Tyr Leu Glu Asn Pro Lys Lys
65                  70                  75                  80

Tyr Ile Pro Gly Thr Lys Met Ala Phe Gly Leu Lys Ala Lys
                85                  90                  95

Asp Arg Asn Asp Leu Val Thr Tyr Leu Leu Ser Ala Thr Lys
            100                 105                 110

<210> SEQ ID NO 12
<211> LENGTH: 110
<212> TYPE: PRT
<213> ORGANISM: Lodderomyces elongisporus

<400> SEQUENCE: 12

Met Pro Ala Pro Tyr Glu Lys Gly Ser Ser Lys Lys Gly Ala Thr Leu
1               5                   10                  15

Phe Lys Thr Arg Cys Leu Gln Cys His Thr Thr Glu Lys Gly Gly Ala
            20                  25                  30

Asn Lys Val Gly Pro Asn Leu His Gly Val Phe Gly Arg His Ser Gly
            35                  40                  45

Gln Ala Glu Gly Tyr Ser Tyr Thr Glu Ala Asn Lys Lys Ala Gly Val
        50                  55                  60

Leu Trp Asp Glu Gln His Met Ser Asp Tyr Leu Glu Asn Pro Lys Lys
65                  70                  75                  80

Tyr Ile Pro Gly Thr Lys Met Ala Phe Ala Gly Leu Lys Lys Ala Lys
                85                  90                  95

Asp Arg Asn Asp Leu Val Thr Tyr Leu Lys Glu Ala Thr Ser
            100                 105                 110

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggatccatgc cagctccata cgaa                                          24

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaattcctat ttggtggcct tggccaa                                       27

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 15
ggatccatga ctgaattcaa ggcc                                    24

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctcgagttac tcacaggctt ttttcaa                                 27

<210> SEQ ID NO 17
<211> LENGTH: 109
<212> TYPE: PRT
<213> ORGANISM: Saccharomyces cerevisiae

<400> SEQUENCE: 17

Met Thr Glu Phe Lys Ala Gly Ser Ala Lys Lys Gly Ala Thr Leu Phe
1               5                   10                  15

Lys Thr Arg Cys Leu Gln Cys His Thr Val Glu Lys Gly Gly Pro His
            20                  25                  30

Lys Val Gly Pro Asn Leu His Gly Ile Phe Gly Arg His Ser Gly Gln
        35                  40                  45

Ala Glu Gly Tyr Ser Tyr Thr Asp Ala Asn Ile Lys Lys Asn Val Leu
    50                  55                  60

Trp Asp Glu Asn Asn Met Ser Glu Tyr Leu Thr Asn Pro Lys Lys Tyr
65                  70                  75                  80

Ile Pro Gly Thr Lys Met Ala Phe Gly Gly Leu Lys Lys Glu Lys Asp
                85                  90                  95

Arg Asn Asp Leu Ile Thr Tyr Leu Lys Lys Ala Cys Glu
            100                 105

<210> SEQ ID NO 18
<211> LENGTH: 113
<212> TYPE: PRT
<213> ORGANISM: Saccharomyces cerevisiae

<400> SEQUENCE: 18

Met Ala Lys Glu Ser Thr Gly Phe Lys Pro Gly Ser Ala Lys Lys Gly
1               5                   10                  15

Ala Thr Leu Phe Lys Thr Arg Cys Gln Gln Cys His Thr Ile Glu Glu
            20                  25                  30

Gly Gly Pro Asn Lys Val Gly Pro Asn Leu His Gly Ile Phe Gly Arg
        35                  40                  45

His Ser Gly Gln Val Lys Gly Tyr Ser Tyr Thr Asp Ala Asn Ile Asn
    50                  55                  60

Lys Asn Val Lys Trp Asp Glu Asp Ser Met Ser Glu Tyr Leu Thr Asn
65                  70                  75                  80

Pro Lys Lys Tyr Ile Pro Gly Thr Lys Met Ala Phe Ala Gly Leu Lys
                85                  90                  95

Lys Glu Lys Asp Arg Asn Asp Leu Ile Thr Tyr Met Thr Lys Ala Ala
            100                 105                 110

Lys

```
<210> SEQ ID NO 19
<211> LENGTH: 113
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (5)..(5)
<223> OTHER INFORMATION: Met or Ser
<220> FEATURE:
<221> NAME/KEY: MOD_RES
<222> LOCATION: (7)..(7)
<223> OTHER INFORMATION: Glu or Gly
<220> FEATURE:
<221> NAME/KEY: MOD_RES
<222> LOCATION: (10)..(10)
<223> OTHER INFORMATION: Ala or Pro
<220> FEATURE:
<221> NAME/KEY: MOD_RES
<222> LOCATION: (25)..(25)
<223> OTHER INFORMATION: Leu or Gln
<220> FEATURE:
<221> NAME/KEY: MOD_RES
<222> LOCATION: (30)..(30)
<223> OTHER INFORMATION: Val or Ile
<220> FEATURE:
<221> NAME/KEY: MOD_RES
<222> LOCATION: (32)..(32)
<223> OTHER INFORMATION: Lys or Glu
<220> FEATURE:
<221> NAME/KEY: MOD_RES
<222> LOCATION: (36)..(36)
<223> OTHER INFORMATION: His or Asn
<220> FEATURE:
<221> NAME/KEY: MOD_RES
<222> LOCATION: (53)..(53)
<223> OTHER INFORMATION: Ala or Val
<220> FEATURE:
<221> NAME/KEY: MOD_RES
<222> LOCATION: (54)..(54)
<223> OTHER INFORMATION: Glu or Lys
<220> FEATURE:
<221> NAME/KEY: MOD_RES
<222> LOCATION: (64)..(64)
<223> OTHER INFORMATION: Lys or Asn
<220> FEATURE:
<221> NAME/KEY: MOD_RES
<222> LOCATION: (68)..(68)
<223> OTHER INFORMATION: Leu or Lys
<220> FEATURE:
<221> NAME/KEY: MOD_RES
<222> LOCATION: (72)..(72)
<223> OTHER INFORMATION: Asn or Asp
<220> FEATURE:
<221> NAME/KEY: MOD_RES
<222> LOCATION: (73)..(73)
<223> OTHER INFORMATION: Asn or Ser
<220> FEATURE:
<221> NAME/KEY: MOD_RES
<222> LOCATION: (93)..(93)
<223> OTHER INFORMATION: Gly or Ala
<220> FEATURE:
<221> NAME/KEY: MOD_RES
<222> LOCATION: (108)..(108)
<223> OTHER INFORMATION: Leu or Met
<220> FEATURE:
<221> NAME/KEY: MOD_RES
<222> LOCATION: (109)..(109)
<223> OTHER INFORMATION: Lys or Thr
<220> FEATURE:
<221> NAME/KEY: MOD_RES
<222> LOCATION: (112)..(112)
<223> OTHER INFORMATION: Cys or Ala
<220> FEATURE:
<221> NAME/KEY: MOD_RES
<222> LOCATION: (113)..(113)
<223> OTHER INFORMATION: Glu or Lys
```

```
-continued

<400> SEQUENCE: 19

Met Ala Lys Glu Xaa Thr Xaa Phe Lys Xaa Gly Ser Ala Lys Lys Gly
1               5                   10                  15

Ala Thr Leu Phe Lys Thr Arg Cys Xaa Gln Cys His Thr Xaa Glu Xaa
            20                  25                  30

Gly Gly Pro Xaa Lys Val Gly Pro Asn Leu His Gly Ile Phe Gly Arg
        35                  40                  45

His Ser Gly Gln Xaa Xaa Gly Tyr Ser Tyr Thr Asp Ala Asn Ile Xaa
        50                  55                  60

Lys Asn Val Xaa Trp Asp Glu Xaa Xaa Met Ser Glu Tyr Leu Thr Asn
65                  70                  75                  80

Pro Lys Lys Tyr Ile Pro Gly Thr Lys Met Ala Phe Xaa Gly Leu Lys
                85                  90                  95

Lys Glu Lys Asp Arg Asn Asp Leu Ile Thr Tyr Xaa Xaa Lys Ala Xaa
            100                 105                 110

Xaa

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 20

Cys Xaa Xaa Cys His
1               5
```